(12) United States Patent
Amasino et al.

(10) Patent No.: US 7,723,565 B2
(45) Date of Patent: May 25, 2010

(54) VERNALIZATION-RELATED MOLECULES AND METHODS FOR INDUCIBLY-CONFERRING EPIGENETIC CHANGES

(75) Inventors: Richard M. Amasino, Madison, WI (US); Si-Bum Sung, Madison, WI (US); Yuehui He, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 372 days.

(21) Appl. No.: 10/905,520

(22) Filed: Jan. 7, 2005

(65) Prior Publication Data

US 2005/0160499 A1   Jul. 21, 2005

Related U.S. Application Data

(60) Provisional application No. 60/534,835, filed on Jan. 7, 2004.

(51) Int. Cl.
*C12N 15/29* (2006.01)
*C12N 15/82* (2006.01)
(52) U.S. Cl. .................... 800/278; 800/290; 435/320.1; 536/23.6
(58) Field of Classification Search ................ 536/23.1, 536/23.6; 800/278, 290, 287
See application file for complete search history.

(56) References Cited

U.S. PATENT DOCUMENTS 5,939,601 A * 8/1999 Klessig et al. ............... 800/279
6,492,575 B1 * 12/2002 Wagner et al. ................ 800/25

OTHER PUBLICATIONS

Wood et al (2006, PNAS 103(39):14631-14636).*
Brucker et al (Planta (2005) 220:864-874).*
Bowie et al, Science 247:1306-1310, 1990.*
McConnell et al, Nature 411 (6838):709-713, 2001.*
Lohmann et al (2001, Cell 105 :793-803).*
Busch et al (1999, Science 285:585-587).*
Aasland, R., Gibson, T.J., & Stewart, A.F.: "The PHD Finger: Implications for Chromatin-Mediated Transcriptional Regulation," Trends. Biochem. Sci. 20: 56-59 (1995).
Burn, J.E., et al.: "DNA Methylation, Vernalization, and the Initiation of Flowering," Proc. Natl. Acad. Sci. USA 90: 287-291 (1993).
Chouard, P.: "Vernalization and its Relations to Dormancy," Annu. Rev. Plant Physiol. 11: 191-238 (1960).
Fair, K., et al.: "Protein Interactions of the MLL PHD Fingers Modulate MLL Target Gene Regulation in Human Cells," Mol. Cell. Biol. 21: 3589-3597 (2001).
Gazzani, S., et al.: "Analysis of the Molecular Basis of Flowering Time Variation in *Arabidopsis* Accessions," Plant Physiol. 132: 1107-1114 (2003).
Gendall, A.R., Levy, Y.Y., Wilson, A, & Dean, C.: "The Vernalization 2 Gene Mediates the Epigenetic Regulation of Vernalization in *Arabidopsis*," Cell 107: 525-535 (2001).
Gozani, O., et al.: "The PHD Finger of the Chromatin-Associated Protein ING2 Functions as a Nuclear Phosphoinositide Receptor," Cell 114: 99-111(2003).
Grewal, S.I.S., & Moazed, D.: "Heterochromatin and Epigenetic Control of Gene Expression," Science 301: 798-801 (2003).
Johanson, U., et al.: "Molecular Analysis of Frigida, a Major Determinant of Natural Variation in *Arabidopsis* Flowering Time," Science 290: 344-347 (2000).
Johnson, L., Cao, X., & Jacobsen, S.: "Interplay Between Two Epigenetic Marks: DNA Methylation and Histone H3 Lysine 9 Methylation," Curr. Biol. 12: 1360-1367(2002).
Kehle, J., et al.: "dMi-2, a Hunchback-Interacting Protein that Functions in Polycomb Repression," Science 282: 1897-1900 (1998).
Kotake, T., et al.: "*Arabidopsis* Terminal Flower 2 Gene Encodes a Heterochromatin Protein 1 Homolog and Represses Both Flowering Locus T to Regulate Flowering Time and Several Floral Homeotic Genes," Plant Cell Physiol. 44: 555-564 (2003).
Lang, A., & Melchers, G.: "Vernalisation und Devernalisation bei einer Zweijahrigen Pflanze," Z. Naturforsch 2b: 444-449 (1947).
Lee, I., et al.: "The Late-Flowering Phenotype of Frigida and Mutations in Luminidependens is Suppressed in the Landsberg *erecta* Strain of *Arabidopsis*," Plant J. 6: 903-909 (1994).
Levy, Y.Y., et al.: "Multiple Roles of *Arabidopsis* VRN1 in Vernalization and Flowering Time Control," Science 297: 243-246 (2002).
Main, A.L., et al.: "The Three-Dimensional Structure of the Tenth Type III Module of Fibronectin: An Insight into RGD-Mediated Interactions," Cell 71: 671-678 (1992).
Michaels, S.D., & Amasino, R.M.: "Flowering Locus C Encodes a Novel MADS Domain Protein that Acts as a Repressor of Flowering," Plant Cell 11: 949-956 (1999).
Michaels, S.D., & Amasino, R.M.: "Memories of Winter: Vernalization and the Competence to Flower," Plant Cell and Environment 23: 1145-1153 (2000).
Michaels, S.D., & Amasino, R.M.: "Loss of Flowering Locus C Activity Eliminates the Late-Flowering Phenotype of Frigida and Autonomous Pathway Mutations but not Responsiveness to Vernalization," Plant Cell 13: 935-941 (2001).
Michaels, S.D., & Amasino, R.M.: "The Gibberellic Acid Biosynthesis Mutant ga1-3 of *Arabidopsis thaliana* is Responsive to Vernalization," Dev. Genet. 25: 194-198 (1999).
Michaels, S.D., et al.: "AGL24 Acts as a Promoter of Flowering in *Arabidopsis* and is Positively Regulated by Vernalization," Plant J. 33: 867-874 (2003).
Michaels, S.D., et al.: "Attenuation of Flowering Locus C Activity as a Mechanism for the Evolution of Summer-Annual Flowering Behavior in *Arabidopsis*," Proc. Natl. Acad. Sci. USA 100:10102-10107 (2003).
Reyes, J.C., et al.: "Chromatin-Remodeling and Memory Factors. New Regulators of Plant Development," Plant Physiol. 130: 1090-1101 (2002).
Richards, E.J., & Elgin, S.C.R.: "Epigenetic Codes for Heterochromatin Formation and Silencing: Rounding up the Usual Suspects," Cell 108: 489-500 (2002).

(Continued)

*Primary Examiner*—Stuart F. Baum
(74) *Attorney, Agent, or Firm*—Quarles & Brady, LLP

(57) ABSTRACT

The invention provides vernalization-related polypeptides, nucleic acids and methods of using the same for inducibly-conferring epigenetic change on a target gene in plant or non-plant settings.

7 Claims, 6 Drawing Sheets

OTHER PUBLICATIONS

Schultz, D.C., et al.: "SETDB1: A Novel KAP-1-Associated Histone H3, Lysine 9-Specific Methyltransferase that Contributes to HP1-Mediated Silencing of Euchromatic Genes by KRAB Zinc-Finger Proteins," Genes Dev. 16: 919-932 (2002).

Sheldon, C.C., et al.: "The FLF MADS Box Gene: A Repressor of Flowering in *Arabidopsis* Regulated by Vernalization and Methylation," Plant Cell 11: 445-458 (1999).

Sheldon, C.C., et al.: "Different Regulatory Regions are Required for the Vernalization-Induced Repression of Flowering Locus C and for the Epigenetic Maintenance of Repression," Plant Cell 14: 2527-2537 (2002).

Sheldon, C.C., et al.: "The Molecular Basis of Vernalization: The Central Role of Flowering Locus C (FLC)," Proc. Natl. Acad. Sci. USA 97: 3753-3758 (2000).

Simpson, G.G., & Dean, C.: "*Arabidopsis*, the Rosetta Stone of Flowering Time?" Science 296: 285-289 (2002).

Sung S., & Amasino, R.M.: "Vernalization in *Arabidopsis thaliana* is Mediated by the PHD Finger Protein VIN 3," Nature 427: 159-163 (2004).

Thomashow, M.F.: "So What's New in the Field of Plant Cold Acclimation? Lots!" Plant Physiol. 125: 89-93 (2001).

Weigel, D., et al.: "Activation Tagging in *Arabidopsis*," Plant Physiol. 122: 1003-1013 (2000).

Wellensiek, S.J.: "Dividing Cells as the Locus for Vernalization," Nature 195: 307-308 (1962).

* cited by examiner

```
AtVIN3      KTIRCLEEEGHIDKSFRERF--LTWYSLRATHREVRVVKI-FVETFMEDLSSLGQQLVDT (Seq. ID No: 9)
BoVIN3      KTIRCLEQEGHIDKSFRERFRFLTWYSLRATHRENRVVKLLFDETFMDDPSSLGQQLVDT (Seq. ID No:10)
            ******:***********  **************:****: *.****:* **********

AtVIN3      FSESILSKRSSTNGVVPAGICLKLWH (Seq. ID No:11)
BoVIN3      FSKCIPSKRSPTTGVV---ICLQH-- (Seq. ID No:12)
            **:.* ****.*.***   ***:
```

ID NO:4; and inducing expression of
VERNALIZATION-RELATED MOLECULES AND METHODS FOR INDUCIBLY-CONFERRING EPIGENETIC CHANGES The present application seeks priority from the U.S. provisional application No. 60/534,835 filed on Jan. 7, 2004, which is incorporated herein by reference for all purposes.

STATEMENT AS TO RIGHTS TO INVENTIONS MADE UNDER FEDERALLY SPONSORED RESEARCH AND DEVELOPMENT

This work was supported in part by a grant from the United States Department of Agriculture—Grant 2000-01459. The government of the United States of America may have certain rights in this invention.

FIELD OF THE INVENTION

The invention generally relates to biological processes resulting in epigenetic change and specifically to vernalization-related polypeptides, nucleic acids and methods of using the same.

BACKGROUND OF INVENTION

In biennials and winter annuals, flowering is typically blocked in the first growing season. Exposure to the prolonged cold of winter, through a process called vernalization, is required to alleviate this block and permit flowering in the second growing season.

Plants have evolved the ability to alter their developmental program in response to environmental stimuli. A major switch in the developmental program is the transition to flowering. In many species the timing of this transition is determined by sensing seasonal changes. Photoperiod and temperature are two main environmental cues that plants monitor to determine the correct time to flower.

Vernalization is a term describing the promotion of flowering after exposure to cold. Specifically, vernalization results in "the acquisition or acceleration of the ability to flower by a chilling treatment" [31]. In other words, after vernalization plants do not necessarily initiate flowering but acquire the competence to do so. In many plant species, vernalization requires long-term exposure to the low temperatures of a typical winter. This is a useful adaptation because many vernalization-requiring species have a winter-annual or biennial habit; the plants begin growing in one season but flower in the spring of the second growing season. The term vernalization is derived from the Latin word vernus, meaning "of the spring". In vernalization-requiring species it is critical that the plants are not "tricked" into flowering in the late autumn season by transient exposure to cold followed by warm conditions; thus the requirement for prolonged cold. Flowering of many vernalization-requiring species is also promoted by long photoperiods and this photoperiod requirement provides another level of assurance that flowering does not occur in late autumn when the days are short.

The physiology of vernalization has been extensively studied since the defining work of Gustav Gassner in early 20th century [discussed in 32]. Grafting and localized cooling studies show that the apical meristem is the site of cold perception during vernalization and that vernalization causes the meristem to become competent to flower [32, 33, 34]. Once meristems have been exposed to prolonged cold, they "remember" that they have been vernalized. This memory is mitotically stable. One of the classic experiments that demonstrated this memory was to vernalize biennial *Hyoscyamus niger* and subsequently grow the vernalized plants in non-inductive photoperiods [discussed in 32]. The vernalized *H. niger* plants were able to remember the prior vernalization for long periods of time and were subsequently able to flower when exposed to inductive photoperiods. Another classic study that demonstrated both the site of vernalization and the memory effect was the in vitro regeneration of plants from various tissues of vernalized *Lunaria biennis* [33, 34]. Only tissues that contained dividing cells (including root meristems) regenerated into vernalized plants. Thus dividing cells (or perhaps cells in which DNA replication is occurring) are a prerequisite for vernalization, and the vernalized state is maintained through tissue culture. This type of experiment has also been done in *Arabidopsis* [35]. The mitotically stable cellular memory illustrates the epigenetic nature of vernalization. Of course it is vital that this memory is lost in the next generation so that the vernalization requirement is re-established.

These classical studies of vernalization raise some interesting questions. How can plants measure long-term cold exposure? For example, why does a week of cold not result in vernalization when 4 weeks does? What is the basis of this mitotically stable cellular memory of vernalization.

Recent genetic and physiological studies of the vernalization pathway in *Arabidopsis* and the identification of components involved in this pathway provide a framework for addressing these intriguing questions. As well, these discoveries provide useful molecules and methods for inducibly conferring epigenetic change beyond the vernalization context. Such, techniques for providing permanent change in gene expression of preselected genes would be widely welcomed in a variety of fields, including agriculture and pharmaceutical sciences.

SUMMARY OF INVENTION

The present invention is based on the inventors' discovery of a novel polypeptide, VIN3, and its role in a biological activity conferring epigenetic change, namely a stable repressed chromatin state, on particular target sequences.

In one embodiment, the present invention provides an isolated nucleic acid comprising a nucleotide sequence encoding the VIN3 amino acid sequence set forth in SEQ ID NO:3.

In a preferred embodiment, the isolated nucleic acid sequence is SEQ ID NO: 1. Yet another embodiment of the present invention provides an isolated nucleic acid consisting of the nucleotide sequence set forth in SEQ ID NO:2, which represents the genomic DNA encoding VIN3.

Another embodiment of the invention provides an isolated polypeptide comprising an amino acid sequence at least 90% homologous to the VIN3 amino acid sequence set forth in SEQ ID NO:3.

The present invention further encompasses methods of inducibly-conferring epigenetic repression on a target gene in a plant. Such methods comprise steps of: providing a plant including: (1) an isolated nucleic acid according to SEQ ID NO: 1 or 2 encoding a VIN3 polypeptide under control of an inducible promoter; and (2) a target gene comprising nucleotide sequence set derived from Intron 1 of the FLOWERING LOCUS C forth in SEQ ID NO:4; and inducing expression of the isolated nucleic acid such that VIN3-mediated epigenetic repression of the target gene is effectuated. In a preferred embodiment, the repression of said target gene results in alleviation of a vernalization response in the plant. The plant is preferably a winter annual, biennial plant or Cruciferous plant. In a preferred embodiment, the target gene is FLOWERING LOCUS C(FLC) or a homolog thereof.

Another embodiment of the present invention provides in vivo methods for inducibly-conferring epigenetic change on a target gene by a VIN3-mediated process. Such a method comprises the steps of: (1) providing a target gene including a nucleotide sequence derived from Intron 1 of Flowering Locus C as set forth in SEQ ID NO:4; and (2) inducing a VIN3-mediated process resulting in an epigenetic change on said target gene wherein said epigenetic change is characterized by a stable repressed chromatin state.

Other objects, features and advantages of the present invention will become apparent after review of the specifications, claims and drawings.

DETAILED DESCRIPTION OF THE INVENTION

GENERAL

Figure 1:
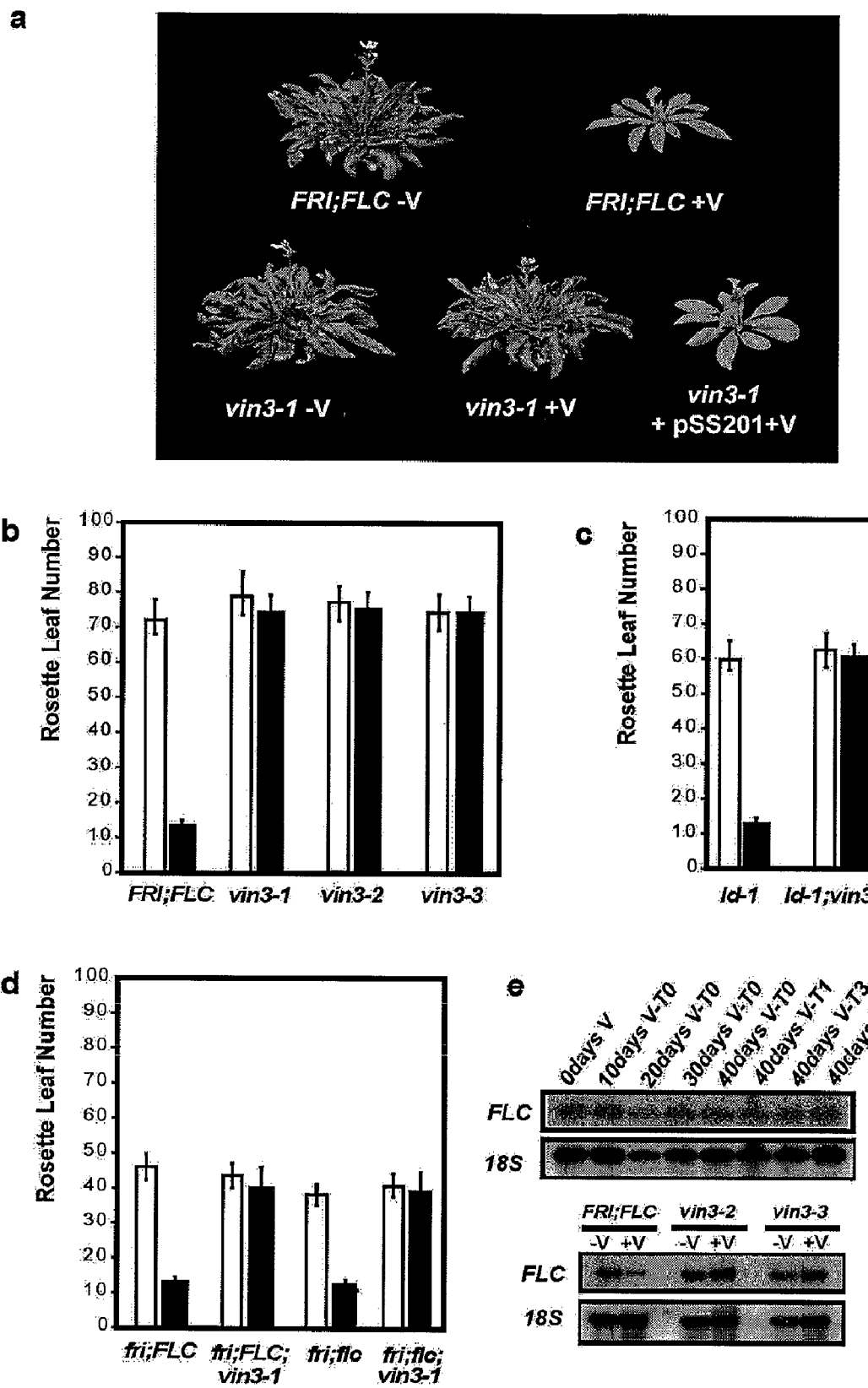
FIG. 1. Characterization of vernalization-insensitive 3 mutants. a, vin3 blocks the vernalization response. Top: parental winter-annual line with and without vernalization. Bottom: vin1-3 mutant with (+V) and without (−V) vernalization and rescue of vin3-1 with a VIN3 transgene. b, Block of the vernalization response in vin3 mutants. White bars: leaf number at flowering of non-vernalized plants; solid bars: values for plants vernalized for 40 days as described[6]. c, vin3 causes vernalization insensitivity in the luminidependens mutant. d, vin3 blocks the vernalization response in a flc mutant in short days. e, FLC is not repressed by vernalization in vin3 mutants. Top panel: length of exposure to 2-4° C. is days V. T0 samples were harvested directly from cold-grown plants. T1, T3 and T7 indicate the number of days the plants were grown at 22° C. after 40 days of cold. Bottom panel: +V samples were vernalized for 40 days and followed by 7 days at 22° C.

Before the present polypeptides, nucleic acids, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells, reference to the "vector" is a reference to one or more vectors and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the polypeptides, polynucleotides, cell lines, vectors, and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Cell Culture and Somatic Cell Genetics of Plants, Vol. 1 (I. K. Vasil, ed. 1984); R. V. Stanier, J. L. Ingraham, M. L. Wheelis, and P. R. Painter, The Microbial World, (1986) 5th Ed. Prentice-Hall.

II. Definitions

Figures 5, 6:
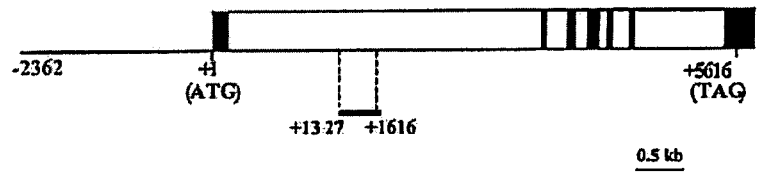
FIG. 5. Amino acid homology between partial sequences of *A. thaliana* VIN3 and a putative homolog identified by the inventors in *Brassica oleracea*.
FIG. 6. Schematic of Flowering Locus C(FLC) illustrating relative position of Intron 1 sequence 1327-1616 to which VIN3-mediated epigenetic change is directed.

"VIN3", as used herein, refers to the amino acid sequences of the VIN3 protein obtained from *A. thaliana*. In addition, VIN3 shall also refer to the amino acid sequences of VIN3 obtained from any species (i.e., orthologs), (e.g. other strains of *A. thaliana*, and the like), from any source whether natural, synthetic, semi-synthetic, or recombinant. FIG. 5 depicts amino acid sequence comparison between *A. thaliana* VIN3 and a putative homolog from *B. oleracea*. The term encompasses proteins encoded by nucleotide sequences representing allelic variants as well as those containing single nucleotide polymorphisms (SNPs).

"vin3", as used herein, refers to the nucleotide sequences of the vin3 gene obtained from *A. thaliana*. In addition, vin3 shall also refer to the nucleotide sequences of the vin3 gene obtained from any species, (e.g. other strains of *A. thaliana*, and the like), from any source whether natural, synthetic, semi-synthetic, or recombinant. The term encompasses allelic variants and single nucleotide polymorphisms (SNPs).

"SEQ ID NO:1", set forth in its entirety in the Sequence Listing, refers to cDNA isolated from *A. thaliana* which is 1803 nucleotides in length and encompasses the nucleotide sequence encoding the VIN3 protein.

"SEQ ID NO:2" refers to a nucleotide sequence from genomic DNA isolated from *A. thaliana* which is 2232 nucleotides in length and encompasses coding sequence for the VIN3 protein. SEQ ID NO:2 is set forth in its entirety in the Sequence Listing.

"SEQ ID NO:3" refers to an amino acid sequence encoding the VIN3 protein of 600 amino acids in length as isolated from *A. thaliana* and set forth in the Sequence Listing.

"SEQ ID NO:4" refers to partial DNA sequence for INTRON1 of FLOWERING LOCUS C(FLC) from *A. thaliana*. This is the region identified by the present inventors to be targeted by VIN3 mediated processes resulting in epigenetic change.

"SEQ ID NO: 5" refers to cDNA sequence of FLC from *A. thaliana*.

"SEQ ID NO:6" refers to genomic sequence of FLC from *A thaliana*.

An "allele" or "allelic sequence", as used herein, is an alternative form of the gene encoding VIN3. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Amino acid sequence", as used herein, refers to an oligopeptide, peptide, polypeptide, or protein sequence, and fragment thereof. Where "amino acid sequence" is recited herein to refer to a particular amino acid sequence (e.g., the amino acid sequence set forth in SEQ ID NO:3), "amino acid sequence", and like terms, are not meant to limit the amino acid sequence to the complete amino acid sequence referenced but shall be understood to include fragments of the complete amino acid sequence. The term shall further encompass synthetic molecules as well as those occurring naturally. The term "portion" or "fragment", as used herein, with regard to an amino acid sequence (as in "a fragment of SEQ ID NO:3"), specifically refers to segments of that amino acid sequence which are not naturally occurring as fragments and would not be found in the natural state. The segments may range in size from five amino acid residues to the entire amino acid sequence minus one amino acid. Thus, a polypeptide "comprising at least a portion of the amino acid sequence of SEQ ID NO:3" or "including an amino acid sequence as set forth in SEQ ID NO:3 or fragments thereof" encompasses the full-length VIN3 amino acid sequences and segments thereof.

The term "biologically active", as used herein, refers to a protein, polypeptide, amino acid sequence, or nucleotide sequence encoding a product having structural, regulatory, or biochemical functions of a naturally occurring molecule. Preferably, a biologically active fragment of VIN3 will have the epigenetic switching capabilities of a naturally occurring VIN3 molecule disclosed herein.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementary between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

The term "homology", as used herein, refers to sequence similarity between two peptides or between two nucleic acid molecules. Homology may be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementary (e.g., less than about 30% identity). In the absence of non-specific binding, the probe will not hybridize to the second non-complementary target sequence. In the art, "identity" means the degree of sequence relatedness between polypeptide or polynucleotide sequences, as the case may be, as determined by the match between strings of such sequences. "Identity" and "homology" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and homology are codified in publicly available computer programs. Preferred computer program methods to determine identity and homology between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al, NCBI NLM NIH Bethesda, Md. 20894; Altschul, S., et al., J. Mol. Biol. 215: 403-410 (1990). The well known Smith Waterman algorithm may also be used to determine identity.

The term "hybridization", as used herein, refers to any process by which a strand of nucleic acid binds with a complementary strand through base pairing.

"Isolated" or "purified" or "isolated and purified" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living. As so defined, "isolated nucleic acid" or "isolated polynucleotide" includes nucleic acids integrated into a host cell chromosome at a heterologous site, recombinant fusions of a native fragment to a heterologous sequence, recombinant vectors present as episomes or as integrated into a host cell chromosome. As used herein, the term "substantially purified", refers to nucleic or amino acid sequences that are removed from their natural environment, isolated or separated, and are at least 60% free, preferably 75% free, and most preferably 90% free from other components with which they are naturally associated. As used herein, an isolated nucleic acid "encodes" a reference polypeptide when at least a portion of the nucleic acid, or its complement, can be directly translated to provide the amino acid sequence of the reference polypeptide, or when the isolated nucleic acid can be used, alone or as part of an expression vector, to express the reference polypeptide in vitro, in a prokaryotic host cell, or in a eukaryotic host cell.

"Nucleic acid sequence" or "nucleotide sequence" or polynucleotide sequence", as used herein, refers to an oligonucleotide, nucleotide, or polynucleotide, and fragments thereof, and to DNA or RNA of genomic or synthetic origin which may be single- or double-stranded, and represent the sense or antisense strand. Where "nucleic acid sequence" or "nucleotide sequence" or polynucleotide sequence" is recited herein to refer to a particular nucleotide sequence (e.g., the nucleotide sequence set forth in SEQ ID NO:2), "nucleotide sequence", and like terms, are not meant to limit the nucleotide sequence to the complete nucleotide sequence referenced but shall be understood to include fragments of the complete nucleotide sequence. In this context, the term "fragment" may be used to specifically refer to those nucleic acid sequences which are not naturally occurring as fragments and would not be found in the natural state. Generally, such fragments are equal to or greater than 15 nucleotides in length, and most preferably includes fragments that are at least 60 nucleotides in length. Such fragments find utility as, for example, probes useful in the detection of nucleotide sequences encoding VIN3.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variations on the traditional peptide linkage joining the amino acids making up the polypeptide. Where the terms are recited herein to refer to a polypeptide, peptide or protein of a naturally occurring protein molecule, the terms are not meant to limit the polypeptide, peptide or protein to the complete, native amino acid sequence associated with the recited protein molecule but shall be understood to include fragments of the complete polypeptide. The term "portion" or "fragment", as used herein, with regard to a protein or polypeptide (as in "a fragment of the VIN3 polypeptide") refers to segments of that polypeptide which are not naturally occurring as fragments in nature. The segments may range in size from five amino acid residues to the entire amino acid sequence minus one amino acid. Thus, a polypeptide "as set forth in SEQ ID NO:3 or a fragment thereof" encompasses the full-length amino acid sequence set forth in SEQ ID NO:3 as well as segments thereof. Fragments of VIN3 preferably are biologically active as defined herein.

The terms "nucleic acid" or "oligonucleotide" or "polynucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49:1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 141 9), phosphorothioate (Mag et al. (1991) Nucleic Acids Res. 19:1437; and U.S. Pat. No. 5,644,048), phosphorodithioate (Briu et al. (1989) J. Am. Chem. Soc. 111 :2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469, 863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. As used herein, oligonucleotide is substantially equivalent to the terms "amplimers", "primers", "oligomers", and "probes", as commonly defined in the art.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

Expression "control sequences" or "regulatory elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes part I chapter 2 Overview of principles of hybridization and the strategy of nucleic acid probe assays*, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1-3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

"Expression vectors" are defined herein as nucleic acid sequences that are direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, optionally one or more constitutive or inducible promoters. In preferred embodiments, an expression vector is a replicable DNA construct in which a DNA sequence encoding VIN3 or a fragment thereof is operably linked to suitable control sequences capable of effecting the expression of the products in a suitable host. Control sequences include a transcriptional promoter, an optional operator sequence to control transcription and sequences which control the termination of transcription and translation, and so forth.

A "polymorphism" is a variation in the DNA sequence of some members of a species. A polymorphism is thus said to be "allelic," in that, due to the existence of the polymorphism, some members of a species may have the unmutated sequence (i.e. the original "allele") whereas other members may have a mutated sequence (i.e. the variant or mutant "allele").

"Vernalization" shall refer to the acquisition or acceleration of the ability to flower by a chilling treatment.

As used herein, a "target gene" shall be any gene in which the epigenetic change-directing sequences of FLC intron 1 have or may potentially be introduced and, via the VIN3-mediated process described herein, a permanent change may be introduced in the modified target gene to affect expression of the same. While no one theory of operation is adopted herein, the permanent change in the target gene is most likely due to histone deacetylation at the target gene which leads to histone methylation and permanent silencing of the target gene as heterochromatin, i.e., the epigenetic change on target gene is characterized by a stable repressed chromatin state. The target gene is therefore rendered incapable of acting as a template for transcription.

As used herein, the "VIN3-mediated process" shall refer to the biological activity identified by the present inventors in which VIN3 participates to produce an epigenetic change in a particular target gene. The methods described herein achieve epigenetic change at selected target genes by directing the VIN3-mediated process to, in a preferred embodiment, the FLC intron 1 sequence set forth in SEQ ID NO:4.

III. The Invention

Screens for mutants that remain late flowering after a long cold treatment can identify genes in the vernalization pathway. In *Arabidopsis* two genes, VERNALIZATION 1 and 2 (VRN1 and VRN2), have been identified this way. The study of vrn1 and vrn2 mutants has revealed an interesting feature of the vernalization mechanism [37, 38]. In these mutants, repression of FLC occurs the same as in wild type during vernalization. However, the repressed state of FLC is not stably maintained in vrn1 and vrn2 upon return to warm conditions. Thus VRN1 and VRN2 are responsible for the stable maintenance of vernalized state, but not for its initial establishment. Lesions in VRN2 also affect FLC chromatin structure [37], suggesting that remodeling of FLC chromatin is part of the vernalization process in *Arabidopsis*. Expression of VRN1 or VRN2 is not regulated by vernalization, and both genes are expressed more broadly than is FLC. This raises the question of how these rather ubiquitously and constitutively expressed genes repress FLC only after a vernalizing cold treatment.

Figure 7:
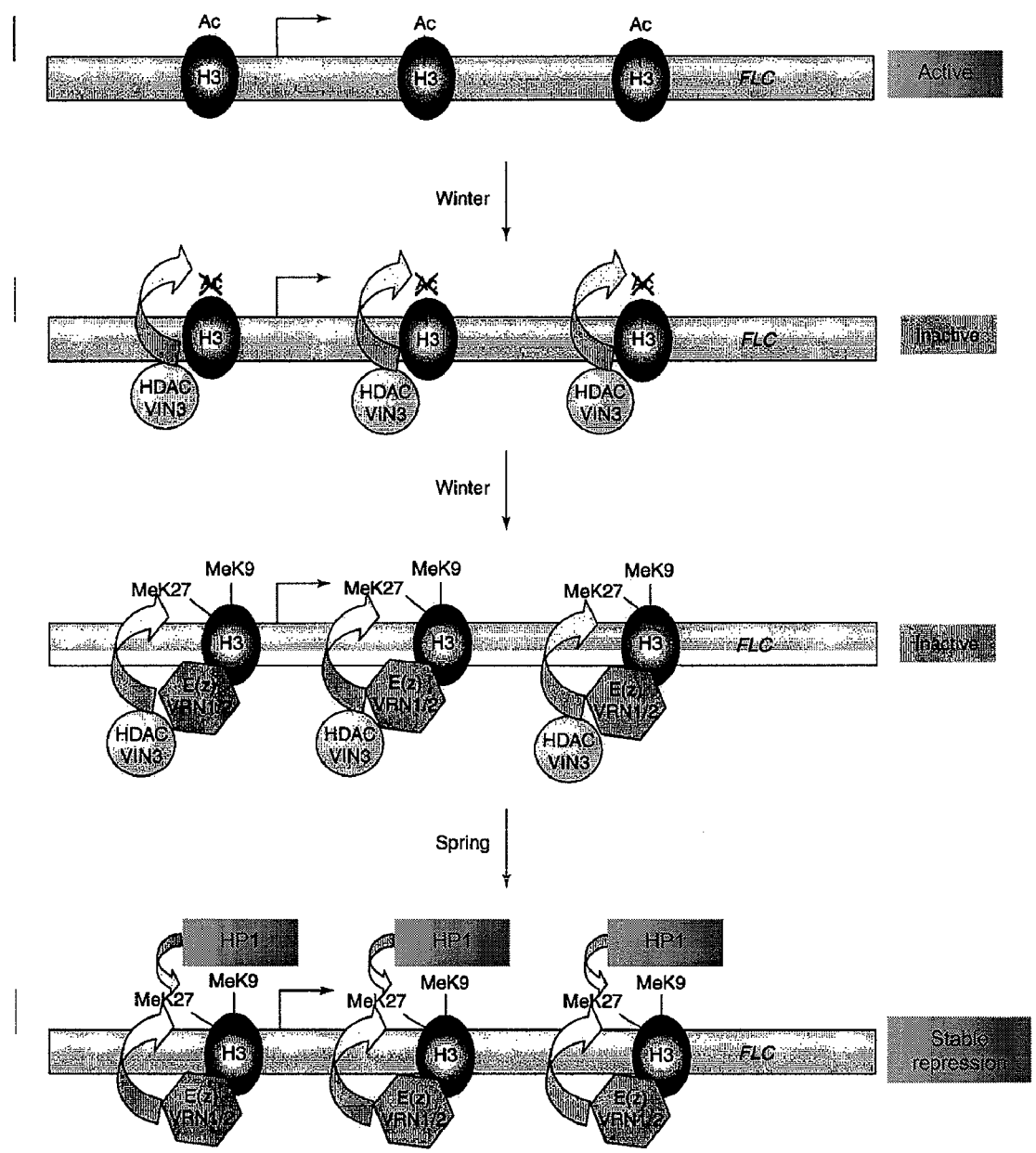
FIG. 7. Hypothetical model of the vernalization-mediated, epigenetic silencing of FLC. During winter, cold-induced expression of VIN3 is necessary for a histone deacetylase (HDAC) complex to de-acetylate H3 in FLC chromatin. De-acetylation in turn creates an environment in which a VRN1-/VRN2-containing complex can methylate H3 at Lys9 as well as at Lys27. By analogy with mammalian and *Drosophila* complexes, the histone-methylating activity of the VRN1/VRN2 complex may be provided by an ENHANCER OF ZESTE [E(z)] homolog [42]. In the spring, VIN3 is no longer expressed and the maintenance of FLC repression requires the continued presence of VRN1 and VRN2, and perhaps other proteins such as HP1, which binds to dimethylated H3 Lys9 [41, 43] and is thought to be involved in the silencing of genes in plant euchromatin [44].

The present inventors' identification of VERNALIZATION INSENSITIVE 3 (VIN3) provides an answer to this question and forms the foundation for novel methods of inducing permanent changes in targeted genes. In vin3 mutants, repression of FLC never occurs, indicating that VIN3 is responsible for initial repression of FLC during cold exposure. Furthermore, expression of VIN3 is only induced by a long period of cold, and as VIN3 is induced, FLC is repressed (FIG. 7a). VIN3 induction by cold is transient; VIN3 mRNA becomes undetectable upon return to warm conditions. The induction of VIN3 occurs predominantly in shoot and root apical meristems—the sites of cold perception and FLC repression in vernalization. This behavior is consistent with a role for VIN3 as a vernalization-specific regulator.

The gene for VIN3 encodes a PHD finger-containing protein. PHD finger motifs are thought to be involved in protein-protein interactions and are often found in various components of chromatin remodeling complexes [39]. The gene for VRN1 encodes Myb-related DNA binding protein. The gene for VRN2 encodes a polycomb group protein which is similar to the *Drosophila* SUPPRESSOR OF ZESTE-12 (Su(z)12). In mammalian system, the Su(z)12 homolog is a component of PRC2 (polycomb repressor complex 2) which has histone methyltransferase activity [40]. This class of polycomb group genes is responsible for stable gene repression by promoting a series of histone modifications [36]. Thus, it is possible that VRN1, VRN2 and VIN3 participate in FLC chromatin remodeling. Indeed, chromatin immunoprecipitation (ChIP) assays using the vin3, vrn2 and vrn1 mutants revealed that vernalization results in a series of FLC chromatin modifications (FIG. 7b).

During vernalization the acetylation levels of specific regions of FLC chromatin decrease and this is followed by an increase of methylation of Histone H3 at Lys9 and Lys27. The evidence for this temporal order of changes comes from studies of the mutants. In vin3, none of the vernalization-mediated histone modifications are observed, suggesting that during vernalization VIN3 is an establishing factor for these chromatin modifications. In vrn2 and vrn1 mutants, hypoacetylation and FLC repression is observed during vernalization, but the hypoacetylation and FLC repression is not maintained upon return to a warm temperature.

Furthermore, none of histone methylations are observed in vrn2 mutants whereas only methylation on Histone H3 at Lys27 is observed in vrn1. These results suggest a model in which VIN3 is involved in the initial FLC repression via hypoacetylation. This hypoacetylated state of FLC chromatin creates a favorable condition for subsequent histone modifications involving VRN1 and VRN2. VRN2 is necessary for methylation of Histone H3 at Lys27 and VRN1 might be involved in methylation of Histone H3 at Lys9. Methylation on Histone H3 at Lys9 is thought to promote stable heterochromatin formation by recruiting heterochromatin protein 1 [40, 41]. Thus vernalization triggers series of histone modifications ultimately resulting in a mitotically stable repressive heterochromatin state that serves as a mechanism to remember winter.

A. VIN3 polypeptides and nucleic acids encoding the same. Based upon the inventors' discoveries, the invention is therefore directed to the polypeptide set forth in SEQ ID NO:3 as well as polypeptides and fragments, particularly those which have the biological activity of VIN3, and also those which have at least 85% identity over their length to a polypeptide of SEQ ID NO:3, and more preferably at least 90% identity over their length to a polypeptide of SEQ ID NO:3, and still more preferably at least 95% identity over their length to a polypeptide of SEQ ID NO:3.

A polypeptide fragment according to the invention is a polypeptide having an amino acid sequence that is entirely the same as part but not all of the amino acid sequence of the aforementioned polypeptides. VIN3 polypeptide fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of SEQ ID NO:3, or of variants thereof, such as a continuous series of residues that includes the amino terminus, or a continuous series of residues that includes the carboxyl terminus. Further preferred are fragments characterized by structural or functional attributes such as fragments that comprise catalytic domains, alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which, as defined herein, are those fragments that mediate activities of epigenetic change, including those with a similar activity or an improved activity, or with a decreased undesirable activity. Particularly preferred fragments are those capable of mediating histone deacetylation associated with sequences of the FLC locus. Also useful are those fragments that are antigenic or immunogenic in an animal, especially in a human. Fragments of the polypeptides of the invention may be employed for producing the corresponding full-length polypeptide by peptide synthesis; therefore, these particular fragments may be employed as intermediates for producing the full-length polypeptides of the invention.

The present invention also encompasses nucleic acids which encode VIN3. Accordingly, any nucleic acid sequence which encodes the amino acid sequence of VIN3 can be used to produce recombinant molecules which express VIN3.

It will be appreciated by those skilled in the art that as a result of the degeneracy of the genetic code, a multitude of nucleotide sequences encoding VIN3, some bearing minimal homology to the nucleotide sequences of any known and naturally-occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring VIN3, and all such variations are to be considered as being specifically disclosed.

Preferred embodiments of the invention are polynucleotides that are at least 70% identical over their entire length to a polynucleotide set out in SEQ ID NO:1, and polynucleotides that are complementary to the same. Alternatively, most highly preferred are polynucleotides that comprise a region that is at least 80% identical over its entire length to a polynucleotide set out in SEQ ID NO:1 and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred, and among these those with at least 98% and at least 99% are particularly highly preferred, with at least 99% being the more preferred.

Although nucleotide sequences which encode VIN3 and its variants are preferably capable of hybridizing to the nucleotide sequence of the naturally occurring VIN3 under appropriately selected conditions of stringency, it may be advantageous to produce nucleotide sequences encoding VIN3 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding VIN3 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode VIN3 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding VIN3 or any fragment thereof.

Also encompassed by the invention are nucleotide sequences that are capable of hybridizing to the claimed nucleic acids, and in particular, those that encode the amino acid sequence set forth in SEQ ID NO:3, under various conditions of stringency as taught in Wahl, G. M. and S. L. Berger (1987; Methods Enzymol. 152:399-407) and Kimmel, A. R. (1987; Methods Enzymol. 152:507-511), preferably highly stringent hybridization conditions, as defined herein.

Methods for DNA sequencing which are well known and generally available in the art and may be used to practice any of the embodiments of the invention. The methods may employ such enzymes as the Klenow fragment of DNA polymerase 1, SEQUENASE™ (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Me.) and the ABI Catalyst and 373 and 377 DNA Sequencers (Perkin Elmer).

The nucleic acid sequences encoding VIN3 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68°-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111-119). In this method, multiple restriction enzyme digestions and ligations may also be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055-3060). Additionally, one may use PCR, nested primers, and PROMOTER FINDER™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, nucleotide sequences or fragments thereof which encode VIN3 may be used in recombinant DNA molecules to direct expression of VIN3, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express VIN3.

As will be understood by those of skill in the art, it may be advantageous to produce VIN3-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter VIN3-encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding VIN3 may be ligated to a heterologous sequence to encode a fusion protein. For example, to screen peptide libraries for inhibitors of VIN3 activity, it may be useful to encode a chimeric VIN3 protein that can be recognized by a commercially available antibody. A fusion protein may also be engineered to contain a cleavage site located between the VIN3 encoding sequence and the heterologous protein sequence, so that VIN3 may be cleaved and purified away from the heterologous moiety.

In another embodiment, sequences encoding VIN3 may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the protein itself may be produced using chemical methods to synthesize the amino acid sequence of VIN3, or a fragment thereof. For example, peptide synthesis can be performed using various solid-phase techniques (Roberge, J. Y. et al. (1995) Science 269:202-204) and automated synthesis may be achieved, for example, using the ABI 431A Peptide Synthesizer (Perkin Elmer).

In order to express a biologically active VIN3, the nucleotide sequences encoding VIN3 or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding VIN3 and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding VIN3. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding VIN3, vectors based on SV40 or EBV may be used with an appropriate selectable marker.

In bacterial systems, a number of expression vectors may be selected depending upon the use intended for VIN3. For example, when large quantities of VIN3 are needed for the induction of antibodies, vectors which direct high level expression of fusion proteins that are readily purified may be used. Such vectors include, but are not limited to, the multifunctional E coli cloning and expression vectors such as BLUESCRIPT™ (Stratagene), in which the sequence encoding VIN3 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503-5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

In cases where plant expression vectors are used, the expression of sequences encoding VIN3 may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

Host cells which contain the nucleic acid sequence encoding VIN3 and express VIN3 may be identified by a variety of procedures known to those of skill in the art. These procedures include, but are not limited to DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding VIN3 can be detected by DNA-DNA or DNA-RNA hybridization or amplification using probes or fragments or fragments of polynucleotides encoding VIN3. Nucleic acid amplification based assays involve the use of oligonucleotides or oligomers based on the sequences encoding VIN3 to detect transformants containing DNA or RNA encoding VIN3.

A variety of protocols for detecting and measuring the expression of VIN3, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on VIN3 is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding VIN3 include oligolabeling, nick translation, end-labeling or PCR amplification using a labeled nucleotide. Alternatively, the sequences encoding VIN3, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding VIN3 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode VIN3 may be designed to contain signal sequences which direct secretion of VIN3 through a prokaryotic or eukaryotic cell membrane. Other constructions may be used to join sequences encoding VIN3 to nucleotide sequence encoding a polypeptide domain which will facilitate purification of soluble proteins Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and VIN3 may be used to facilitate purification. One such expression vector provides for expression of a fusion protein containing VIN3 and a nucleic acid encoding 6 histidine residues preceding a thioredoxin or an enterokinase cleavage site. The histidine residues facilitate purification on IMAC (immobilized metal ion affinity Chromatography as described in Porath, J. et al. (1992, Prot. Exp. Purif. 3:263-281) while the enterokinase cleavage site provides a means for purifying VIN3 from the fusion protein. A discussion of vectors which contain fusion proteins is provided in Kroll, D. J. et al. (1993; DNA Cell Biol. 12:441-453).

In addition to recombinant production, fragments of VIN3 may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using Applied Biosystems 431A Peptide Synthesizer (Perkin Elmer). Various fragments of VIN3 may be chemically-synthesized separately and combined using chemical methods to produce the full length molecule.

B. Methods of Inducing VIN3-Mediated Epigenetic Change in a Target Gene:

The present invention provides a unique system for inducibly-conferring epigenetic change on a target gene. It is envisioned that the VIN3-mediated process described herein, and the FLC intron 1 sequence targeted thereby, may be applied in heterologous settings in plant or non-plant subjects to achieve permanent change of at least one selected gene. In general, the components carrying out the VIN3-mediated process, including, of course, VIN3, may be transformed into a heterologous host in which a selected gene has been modified by recombination techniques known in the art to contain the epigenetic change-directing sequences of FLC intron 1. VIN3-mediated process components are preferably under control of an inducible promoter(s) thusly allowing the user to direct the timing of epigenetic change, namely stable repressed chromatin, at the selected gene. One of skill in the art, upon reviewing the materials and methods described in this disclosure, will undoubtedly appreciate the myriad uses a system for inducibly-conferring epigenetic change on a selected gene. The system described and claimed herein is believed to represent a breakthrough technology in the area of introducing epigenetic change in selected target genes. Various advantages accompany the invention, not the least of which is the need to use only a transient induction agent to trigger the VIN3-mediated process which leads to a permanent change in gene expression. Thus, it can be envisioned that exposure to a single application of induction agent will lead to a lasting alteration in gene expression for an organism on which the present inventive methods are carried out.

Accordingly, the present invention encompasses methods of inducibly-conferring epigenetic repression on a target gene in a plant. Such methods comprise steps of: providing a plant including: (1) an isolated nucleic acid according to SEQ ID NO: 1 or 2 encoding a VIN3 polypeptide under control of an inducible promoter; and (2) a target gene comprising nucleotide sequence from Intron I of FLC set forth in SEQ ID NO:4; and inducing expression of said isolated nucleic acid such that VIN3-mediated epigenetic repression of the target gene is effectuated. In a preferred embodiment, the repression of said target gene results in alleviation of a vernalization response in the plant. The plant is preferably a winter annual, biennial plant or Cruciferous plant. In a preferred embodiment, the target gene is FLOWERING LOCUS C(FLC) or a homolog thereof.

Another embodiment of the present invention provides in vivo methods for inducibly-conferring epigenetic change on a target gene by a VIN3-mediated process. Such a method comprises the steps of: (1) providing a target gene including a nucleotide sequence derived from Intron 1 of Flowering Locus C as set forth in SEQ ID NO:4; and (2) inducing a VIN3-mediated process resulting in an epigenetic change on said target gene wherein said epigenetic change is characterized by a stable repressed chromatin state. Such methods may be conveniently carried out in plant and non-plant heterologous systems.

A myriad of plant promoters have been described with various expression characteristics, which may be useful in directing expression of VIN3 or homologs thereof in carrying out methods according to the invention. Examples of some constitutive promoters which have been described include the CaMV 35S (Odell et al., 1985), CaMV 19S (Lawton et al., 1987), nos (Ebert et al, 1987), rice actin 1 (Wang et al., 1992; U.S. Pat. No. 5,641,876), and Adh (Walker et al., 1987), rice actin (McElroy et al., (1990), Plant Cell, 163-171); ubiquitin (Christensen et al., (1992), Plant Mol. Biol. 12:619-632; and Christensen, et al., (1992), Plant Mol. Biol. 18:675-689); pEMU (Last, et al., (1991), Theor. Appl. Genet. 81:581-588); MAS (Velten et al., (1984), EMBO J. 3:2723-2730); and maize H3 histone (Lepetit et al., (1992), Mol. Gen. Genet. 231:276-285; and Atanassvoa et al., (1992), Plant Journal 2(3): 291-300). The ALS promoter, a Xba/NcoI fragment 5" to the Brassica napus ALS3 structural gene, or a nucleotide sequence having substantial sequence similarity to the XbaI/NcoI fragment, represents a particularly useful constitutive promoter, and is described in published PCT Application WO 96/30530.

Examples of tissue specific promoters which have been described include lectin (Vodkin et al., 1983; Lindstrom et al., 1990), corn alcohol dehydrogenase 1 (Vogel et al., 1989; Dennis et al., 1984), corn light harvesting complex (Simpson, 1986; Bansal et al., 1992), corn heat shock protein (Odell et al., 1985; Rochester et al, 1986), pea small subunit RuBP carboxylase (Poulsen et al, 1986; Cashmore et al, 1983), Ti plasmid mannopine synthase (Langridge et al., 1989), Ti plasmid nopaline synthase (Langridge et al., 1989), petunia chalcone isomerase (Van Tunen et al, 1988), bean glycine rich protein 1 (Keller et al., 1989), truncated CaMV 35S (Odell et al, 1985), potato patatin (Wenzler et al., 1989), root cell (Conkling et al., 1990), maize zein (Reina et al., 1990; Kriz et al., 1987; Wandelt and Feix, 1989; Langridge and Feix, 1983; Reina et al., 1990), globulin-1 (Belanger and Kriz, 1991), α-tubulin, cab (Sullivan et al., 1989), PEPCase (Hudspeth & Grula, 1989), sucrose synthase (Yang & Russell, 1990), R gene complex-associated promoters (Chandler et al, 1989), chalcone synthase promoters (Franken et al., 1991) and vegetative storage protein (VSP) (Guenoune, D., et al., Transgenic Research 12:123-126 (2003); Guerineau, F., et al., Journal of Experimental Botany 54:1153-1162 (2003)).

Inducible promoters which have been described include ABA- and turgor-inducible promoters, the promoter of the auxin-binding protein gene (Schwob et al., 1993), the UDP glucose flavonoid glycosyl-transferase gene promoter (Ralston et al., 1988); the MPI proteinase inhibitor promoter (Cordero et al., 1994), and the glyceraldehyde-3-phosphate dehydrogenase gene promoter (Kohler et al., 1995; Quigley et al., 1989; Martinez et al., 1989). A particularly preferred inducible promoter system for use in the present method is the alcohol dehydrogenase system. The system transferred into plants uses the alcR gene, which encodes the transcriptional activator protein AlcR, and the alcA promoter. The alcR gene is under the control of a strong constitutive promoter such as CaMV 35S. In the absence of the inducer, the transactivator protein AlcR cannot bind the specific sequences of the modified alcA promoter, which is linked to a gene of interest. The modified or chimeric target promoter comprises the regulatory sequences of the alcA promoter and a core promoter region (a TATA box and a transcription start site) of a plant-expressible gene promoter. See following references for details: http://www.cambiaip.org/Whitepapers/Transgenic/Promoters/promoters.html, Hairul A Roslan, Michael G Salter, Chris D Wood, Michael R H White, Kevan P Croft, Frances Robson, George Coupland, John H Doonan, Patrick Laufs, A Brian Tomsett and Mark X Caddick (2001) Characterisation of the ethanol inducible alc gene expression system in Arabidopsis thaliana. The Plant Journal 28 (2) 225-237; M G Salter, J A Paine, K V Riddell, I Jepson, A J Greenland, M X Caddick and A B Tomsett (1998) Characterisation of the ethanol-inducible alc gene expression system for transgenic plants. The Plant Journal 16 127-132; M X Caddick, K V Riddell, A B Tomsett, A J Greenland and W Schuch Synthetic gene promoter and a chemically inducible plant gene expression cassette. British Patent WO93/21334A. The University of Liverpool and ZENECA Seeds. 1992.

A class of genes which are expressed in an inducible manner are glycine rich proteins. Expression of glycine rich proteins is induced by the plant hormone abscibic acid (ABA). Genes encoding glycine rich proteins have been described, for example, from maize (Didierjean et al., 1992; Gomez et al., 1988; Baysdorfer, Genbank Accession No. AF034945) sorghum (Cretin and Puigdomenech, 1990), and rice (Lee et al., Genbank Accession No. AF009411).

In addition to the use of a particular promoter, expression of transgenes can be influenced by other types of elements. In particular, introns have demonstrated the potential for enhancing transgene expression. For example, Callis et al. (1987) described an intron from the corn alcohol dehydrogenase gene which is capable of enhancing the expression of transgenes in transgenic plant cells. Similarly, Vasil et al. (1989) described an intron from the corn sucrose synthase gene having similar enhancing activity. The rice actin 1 intron, in particular, has found wide use in the enhancement of transgene expression in a number of different transgenic crops (McElroy et al., 1991). This 5' intron was identified from the first coding exon of the rice actin 1 sequence (McElroy et al., 1990a). Plant actin is encoded by a gene family present in all plant species studied to date (Meagher, 1991). In rice, there are at least eight actin-like sequences per haploid genome. Four of the rice actin coding sequences (rice actin 1, 2, 3 and 7) have been isolated and shown to differ from each other in the tissue and stage-specific abundance of their respective transcripts (Reece. 1988; McElroy et al., 1990a; Reece et al, 1990; U.S. Pat. No. 5,641,876; Genbank Accession numbers X15865, X15864, X15862, and X15863, respectively).

Plant signal sequences, including, but not limited to, signal-peptide encoding DNA/RNA sequences which target proteins to the extracellular matrix of the plant cell (Dratewka-Kos, et al., (1989), J. Biol. Chem. 264:4896-4900), the *Nicotiana plumbaginifolia* extension gene (DeLoose, et al., (1991), Gene 99:95-100), signal peptides which target proteins to the vacuole like the sweet potato sporamin gene (Matsuka, et al., (1991), PNAS 88:834) and the barley lectin gene (Wilkins, et al., (1990), Plant Cell, 2:301-313), signal peptides which cause proteins to be secreted such as that of PRIb (Lind, et al., (1992), Plant Mol. Biol. 18:47-53), or the barley alpha amylase (BAA) (Rahmatullah, et al. "Nucleotide and predicted amino acid sequences of two different genes for high-pi alpha-amylases from barley." Plant Mol. Biol. 12:119 (1989) and hereby incorporated by reference), or from the present invention the signal peptide from the ESP1 or BEST1 gene, or signal peptides which target proteins to the plastids such as that of rapeseed enoyl-Acp reductase (Verwaert, et al., (1994), Plant Mol. Biol. 26:189-202) are useful in the invention.

The present invention is certainly envisioned to provide methods applicable to a broad range of organisms. In preferred aspects, the organism is a plant. Numerous methods for introducing foreign genes into plants are known and can be used to insert an expression construct/transgenic cassette into a plant host, including biological and physical plant transformation protocols. See, for example, Miki et al., (1993), "Procedure for Introducing Foreign DNA into Plants", In: Methods in Plant Molecular Biology and Biotechnology, Glick and Thompson, eds., CRC Press, Inc., Boca Raton, pages 67-88. The methods chosen vary with the host plant, and include chemical transfection methods such as calcium phosphate, microorganism-mediated gene transfer such as *Agrobacterium* (Horsch, et al., (1985), Science 227:1229-31), electroporation, micro-injection, and biolistic bombardment. See e.g. Rhodes, C. A., et al. (1988) Science 240: 204-207; Shigekawa, K. and Dower, W. J. (1988) BioTechniques 6: 742-751; Sanford, J. C., et al. (1987) Particulate Science & Technology 5:27-37; and McCabe, D. E. (1988) BioTechnology 6:923-926. Expression cassettes and vectors and in vitro culture methods for plant cell or tissue transformation and regeneration of plants are known and available. See, for example, Gruber, et al., (1993), "Vectors for Plant Transformation" In: Methods in Plant Molecular Biology and Biotechnology, Glick and Thompson, eds. CRC Press, Inc., Boca Raton, pages 89-119.

The most widely utilized method for introducing an expression vector into plants is based on the natural transformation system of *Agrobacterium*. *A. tumefaciens* and *A. rhizogenes* are plant pathogenic soil bacteria which genetically transform plant cells. The Ti and Ri plasmids of *A. tumefaciens* and *A. rhizogenes*, respectfully, carry genes responsible for genetic transformation of plants. See, for example, Kado, (1991), Crit. Rev. Plant Sci. 10: 1. Descriptions of the *Agrobacterium* vector systems and methods for *Agrobacterium*-mediated gene transfer are provided in Gruber et al., supra; Miki, et al., supra; and Moloney et al., (1989), Plant Cell Reports 8:238.

Similarly, an expression construct can be inserted into the T-DNA region of a Ti or Ri plasmid derived from *A. tumefaciens* or *A. rhizogenes*. Thus, expression cassettes can be effectively constructed to prepare transgenic plants according to the invention. Many control sequences are known which when coupled to a heterologous coding sequence and transformed into a host organism show fidelity in gene expression with respect to tissue/organ specificity of the original coding sequence. See, e.g., Benfey, P. N., and Chua, N. H. (1989) Science 244: 174-181. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. application Ser. No. 913,914, filed Oct. 1, 1986, as referenced in U.S. Pat. No. 5,262,306, issued Nov. 16, 1993 to Robeson, et al.; and Simpson, R. B., et al. (1986) Plant Mol. Biol. 6: 403-415 (also referenced in the '306 patent); all incorporated by reference in their entirety.

Once constructed, these plasmids can be placed into *A. rhizogenes* or *A. tumefaciens* and these vectors used to transform cells of a variety of plant species. The selection of either *A. tumefaciens* or *A. rhizogenes* will depend on the plant being transformed thereby. In general, *A. tumefaciens* is the preferred organism for transformation. Most dicotyledons, some gymnosperms, and a few monocotyledons (e.g. certain members of the *Liliales* and *Arales*) are susceptible to infection with *A. tumefaciens*. *A. rhizogenes* also has a wide host range, embracing most dicots and some gymnosperms, which includes members of the *Leguminosae, Compositae* and *Chenopodiaceae*. See e.g. Rhodes, C. A., et al. (1988) Science 240: 204-207; Shigekawa, K. and Dower, W. J. (1988) BioTechniques 6: 742-751; Sanford, J. C., et al. (1987) Particulate Science & Technology 5:27-37; and McCabe, D. E. (1988) BioTechnology 6:923-926.

Roots or shoots transformed by inoculation of plant tissue with *A. rhizogenes* or *A. tumefaciens*, containing the expression construct, can be used as a source of plant tissue to regenerate transgenic plants, either via somatic embryogenesis or organogenesis. Examples of such methods for regenerating plant tissue are disclosed in Shahin, E. A. (1985) Theor. Appl. Genet. 69:235-240; U.S. Pat. No. 4,658,082; Simpson, R. B., et al. (1986) Plant Mol. Biol. 6: 403-415; and U.S. patent applications Ser. Nos. 913,913 and 913,914, both filed Oct. 1, 1986, as referenced in U.S. Pat. No. 5,262,306, issued Nov. 16, 1993 to Robeson, et al.; the entire disclosures therein incorporated herein by reference.

Despite the fact that the host range for *Agrobacterium*-mediated transformation is broad, some major cereal crop species and gymnosperms have generally been recalcitrant to this mode of gene transfer, even though some success has recently been achieved in rice (Hiei et al., (1994), The Plant Journal 6:271-282). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 micrometers. The expression vector is introduced into plant tissues with a biolistic device that accelerates the microprojectiles to speeds of 300 to 600 m/s which is sufficient to penetrate the plant cell walls and membranes. (Sanford et al., (1987), Part. Sci. Technol. 5:27; Sanford, 1988, Trends Biotech 6:299; Sanford, (1990), Physiol. Plant 79:206; Klein et al., (1992), Biotechnology 10:268).

Another method for physical delivery of DNA to plants is sonication of target cells as described in Zang et al., (1991), Bio/Technology 9:996. Alternatively, liposome or spheroplast fusions have been used to introduce expression vectors into plants. See, for example, Deshayes et al., (1985), EMBO J. 4:2731; and Christou et al., (1987), PNAS USA 84:3962. Direct uptake of DNA into protoplasts using $CaCl_2$ precipitation, polyvinyl alcohol or poly-L-ornithine have also been reported. See, for example, Hain et al., (1985), Mol. Gen. Genet. 199:161; and Draper et al., (1982), Plant Cell Physiol. 23:451.

Electroporation of protoplasts and whole cells and tissues has also been described. See, for example, Donn et al., (1990), In: Abstracts of the VIIth Int'l. Congress on Plant Cell and Tissue Culture IAPTC, A2-38, page 53; D'Halluin et al., (1992), Plant Cell 4:1495-1505; and Spencer et al., (1994), Plant Mol. Biol. 24:51-61.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

A. Identification of Vernalization Insensitive Mutants

In winter-annual types of *Arabidopsis*, flowering is delayed unless plants are vernalized. The delayed flowering is due to dominant alleles of FRIGIDA (FRI) and FLC[3]. FRI elevates expression of the MADS box transcriptional regulator FLC to levels that suppress flowering[4,5]. Vernalization promotes flowering primarily by repressing FLC expression[4,5,6,7]. The repressed state of FLC is maintained through mitotic cell divisions upon return to warm growing conditions[2]. Many summer-annual accessions of *Arabidopsis* flower rapidly without vernalization because such accessions lack an active FRI allele[8,9] or have a weak FLC allele[9,10] and thus have low levels of FLC expression.

To investigate the molecular mechanism of vernalization, the inventors mutagenized a winter-annual *Arabidopsis* line (the Columbia accession into which an active FRI allele had been introgressed[3]) and screened for mutants that were insensitive to vernalization. In this screen, the inventors found additional alleles of vernalization 1 and 2(vrn1 and vrn2); these genes are necessary to maintain the repressed state of FLC after vernalization[11,12]. The inventors also identified three independent mutants that define a new complementation group, vernalization-insensitive 3 (vin3-1, vin3-2 and vin3-3). In the vin3 mutants, the vernalization response was completely blocked (FIG. 1*a* and *b*).

In *Arabidopsis*, the autonomous pathway defines a group of genes that suppress FLC expression[13]. Autonomous-pathway mutants in a summer-annual background exhibit a vernalization-responsive late-flowering phenotype similar to winter annuals because both have elevated FLC expression prior to vernalization[6,7,13]. The vin3 lesion blocks the vernalization response in the autonomous-pathway mutant luminidependens (FIG. 1*c*). Vernalization also promotes flowering independently of FLC repression; specifically, vernalization can cause more rapid flowering in short days in both wild type and in a flc null mutant[7]. In a vin3 flc double mutant the promotion of flowering by vernalization in short days is prevented (FIG. 1*d*). Thus, VIN3 is required for all situations, both FLC dependent and FLC-independent, in which vernalization can promote flowering. In both the parental winter-annual FRI-containing line and in the summer-annual Col background (fri), the vin3 mutant displayed no pleiotropic phenotypes, and had no effect on flowering other than the block to vernalization (FIG. 1*a,b* and data not shown).

Figure 2:
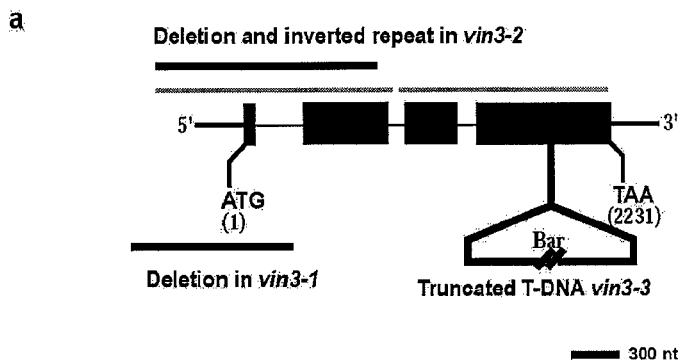
FIG. 2. VIN3 cloning and expression pattern. a, Positions of the domains in VIN3 (PHD finger, fibronectin type III, and (small rectangle) nuclear localization signal) and the lesions in vin3 alleles. vin3-1 is a fast-neutron allele and vin3-2 and vin3-3 are T-DNA insertion alleles. b, RT-PCR analyses of the effect of vernalization on VIN3 and FLC expression in the winter-annual wild type. Samples are as described in FIG. 1e. c, RT-PCR analyses of VIN3 and FLC expression in vrn1. d, Spatial pattern of VIN3 and FLC expression determined by reporter gene (GUS) fusions in wild type without vernalization, after 40 days of vernalization, and after vernalization and 5 days at 22° C. e, FLC expression in vrn1 and vin3. Designations are as in d. 80 VT0 were vernalized for 80 days.
Figure 2:
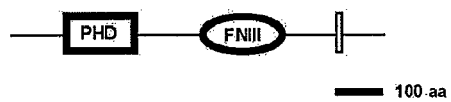
Figure 2:
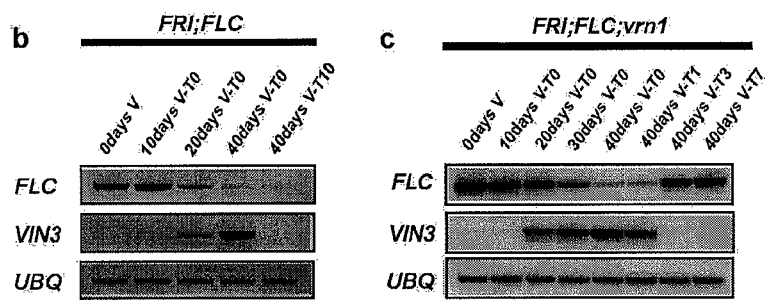
Figure 2:
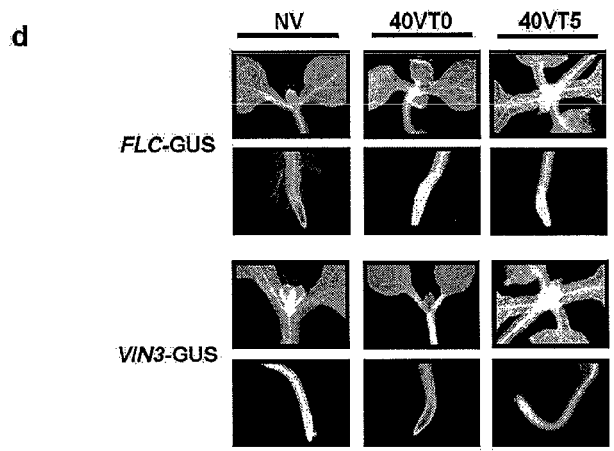
Figure 2:
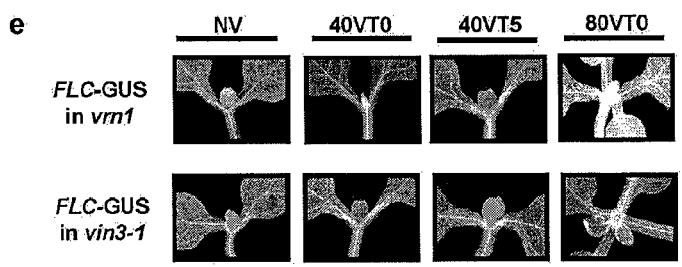

In vin3 mutants, a vernalizing cold treatment is not able to repress FLC expression during and after cold exposure (FIG. 1*e*). This is in contrast to the behavior of vrn1 and vrn2 mutants in which vernalization-mediated FLC repression is observed during the period of cold exposure; i.e., vrn1 and vrn2 behave like wild type with respect to FLC repression during a vernalizing cold treatment, but this repression is not maintained in warm growing conditions (FIG. 2*b,c* and refs. 11 and 12). Thus, unlike VRN1 and VRN2 which are involved in the maintenance of FLC repression, VIN3 plays a role in the establishment of FLC repression during vernalization.

B. Cloning and Characterization of VIN 3 Gene and Polypeptides

The inventors cloned VIN3 by a map-based approach (a rescued line is shown in FIG. 1*a*; the genomic sequence for VIN3 is set forth in SEQ ID NO:2; putative cDNA is set forth in SEQ ID NO:1). VIN3 is comprised of four exons encoding a 600 a.a. protein (SEQ ID NO:3) that contains a putative nuclear localization signal and two domains found in other proteins (FIG. 2*a*): a PHD (plant homeodomain) domain, which is often found in proteins in chromatin remodeling complexes[14], and a FNIII (fibronectin type III) domain, which is often involved in protein-protein interactions[15].

C. Temporal Expression Pattern of VIN3

A requirement for vernalization is an adaptation to ensure that flowering does not occur prior to the onset of winter. To prevent flowering during short-term temperature fluctuations in the fall season, the vernalization process has evolved to distinguish a long exposure to cold from shorter cold exposures[2]. The pattern of VIN3 induction is consistent with a role for VIN3 in the process of distinguishing the duration of cold exposure (FIG. 2*b*). VIN3 is expressed only after a duration of cold exposure that is effective for vernalization, and FLC repression does not occur until VIN3 is induced (FIG. 2*b*). Moreover, the level of VIN3 expression correlates with the duration of cold as well as with the degree of FLC repression; after a long but not vernalization-saturating period of cold exposure, VIN3 is partially induced and FLC is partially repressed (FIG. 2*b*; compare expression levels at 20 versus 40 days of vernalization). In addition, VIN3 mRNA becomes undetectable within three days after return to a warm growth temperature (FIG. 2b,c). Thus, in contrast to VRN1 and VRN2 which are constitutively expressed[11,12], VIN3 is expressed only during cold exposure and the appearance of VIN3 expression is a marker for cold exposures of a duration that are effective for vernalization. VIN3 expression is induced by cold exposure in vrn1 (FIG. 2c) and vrn2 (data not shown) indicating that VIN3 is upstream of VRN1 and VRN2.

D. Spatial Expression Pattern of VIN3

Vernalization causes an epigenetic change that provides competence to flower only in specific tissues such as shoot and root apices[2,16,17]. The pattern of VIN3 expression, determined by a VIN3 promoter fusion to β-Glucuronidase (GUS), matches the regions in which vernalization is effective (FIG. 2d). Furthermore, VIN3 has the same pattern of expression as its target FLC (FIG. 2d). The FLC-GUS construct is subject to repression by vernalization in a wild-type background, whereas in a vin3 mutant FLC-GUS repression does not occur during or after vernalization (FIG. 2e). In contrast, the FLC-GUS construct is repressed in a vrn1 mutant during vernalization (FIG. 2e). The VIN3-GUS construct is expressed only when the plants are exposed to a long period of cold, and expression disappears after the plants are grown in warm conditions (FIG. 2d). Thus the cold and tissue-specific expression of VIN3 is likely to be controlled at the transcriptional level. These results along with the RNA and phenotypic data described above further support a role for VIN3 in the vernalization-mediated establishment of FLC repression in the shoot and root apex.

E. VIN3 Mediated Epigenetic Change; Histone Deacetylation of the FLC Locus

The epigenetic nature of FLC repression by vernalization, and the involvement of proteins related to chromatin-modeling proteins in this process, prompted the inventors to examine whether histone modifications were involved in vernalization-mediated silencing of FLC. In humans and Drosophila, Su(z)12 polycomb group proteins, which are homologs of VRN2, mediate gene silencing by a series of histone modifications leading to methylation of histone H3 at Lys 9[18]. Methylation of Lys 9 is a marker for heterochromatin formation, and H3 Lys 9 methylation is thought to recruit heterochromatin protein 1 (and possibly facilitate DNA methylation) to ensure a mitotically repressed state[19]. During the silencing process, a transiently acting repressor is often required to target specific genes for histone modifications[18]. One of the initial events that requires a transiently acting repressor can be histone de-acetylation[20].

Figure 3:
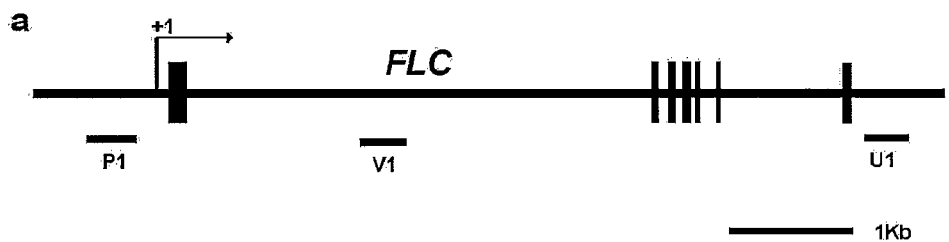
FIG. 3. Chromatin Immunoprecipitation (ChIP) assays in wild type winter-annual *Arabidopsis*. a, Regions of the FLC locus examined (See Methods for details). Coding regions are indicated by vertical lines. b, ChIP using antibodies to modified histones. Samples: non-vernalized (NV), vernalized for 40 days (VT0), or vernalized for 40 days and subsequently grown for 7 days at 22° C. (VT7). Sample preparation was as described[30]. Signal intensities were normalized relative to actin and Ta3 control reactions using ImageQuant, and the fold changes are presented in the bar graphs. c, ChIP using VIN3 and VRN1 antisera. Samples were from plants vernalized for 40 days without exposure to warm temperature. Signal intensities were normalized relative to input signal intensities.
Figure 3:
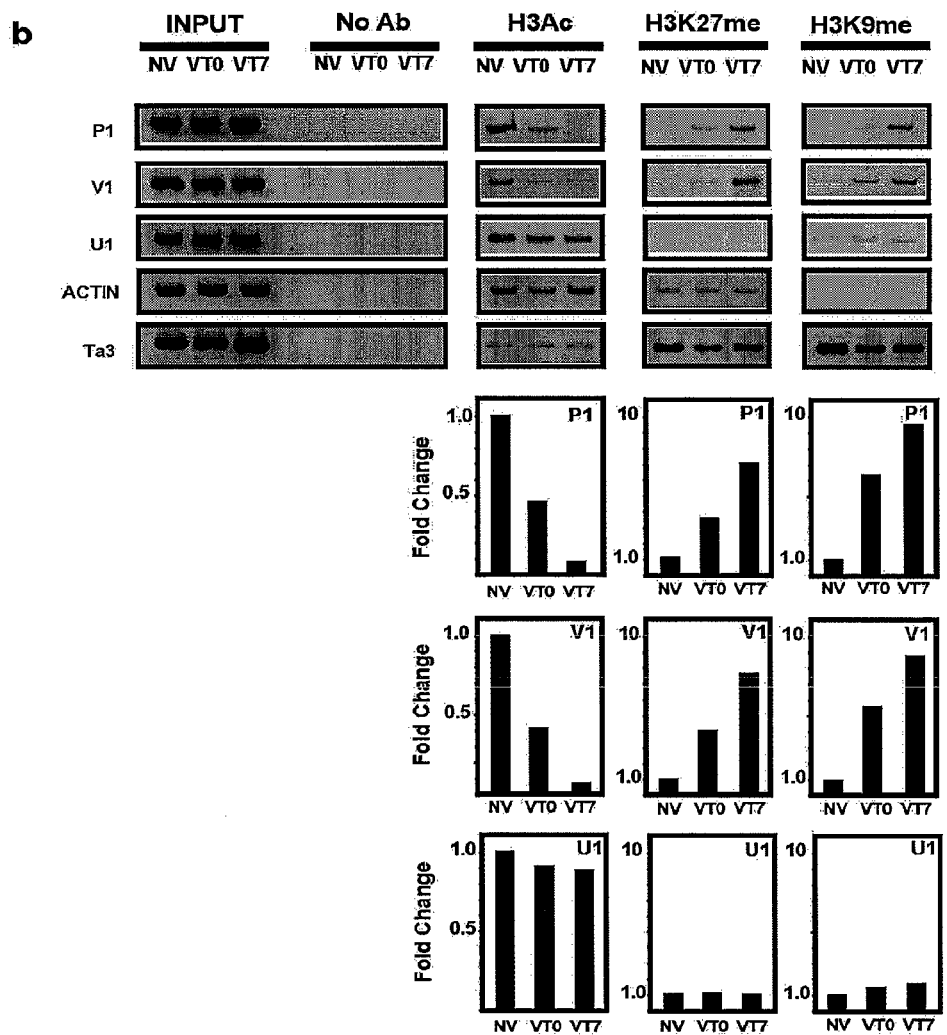
Figure 3:
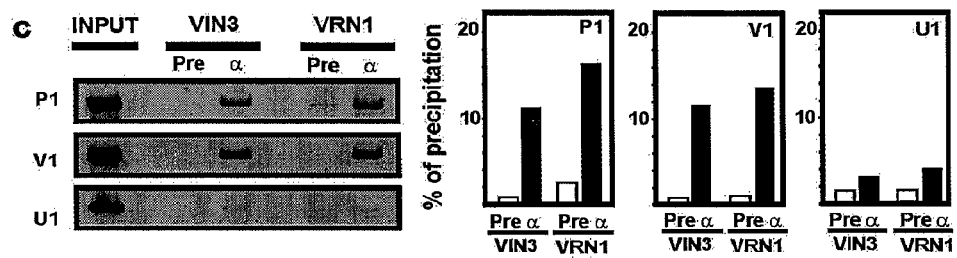

The inventors therefore examined acetylation of histone H3 at Lys 9 and Lys 14 in chromatin of FLC. The inventors observed that a region of intron I (V1) and a region upstream of the transcriptional start site (P1) of FLC exhibited reduced acetylation during vernalization, and upon transfer to warm growing conditions this reduction was maintained (FIG. 3a). FLC chromatin in the region (U1) encoding the 3' UTR however showed little change in acetylation levels. In vin3 the vernalization-mediated changes in FLC acetylation do not occur (FIG. 4a; data shown for the V1 region). In vrn1 and vrn2 reduced acetylation of FLC occurs during vernalization, but this reduction is not maintained in warm growing conditions (FIG. 4a,b). The lack of changes in FLC histone acetylation patterns in vin3 mutants and the transient cold-specific expression of VIN3 in wild type as well as in vrn1 and vrn2 during vernalization indicates that VIN3 participates in a transient repression of FLC that involves histone de-acetylation, and that this VIN3-mediated process is required for the establishment of FLC silencing.

Figure 4:
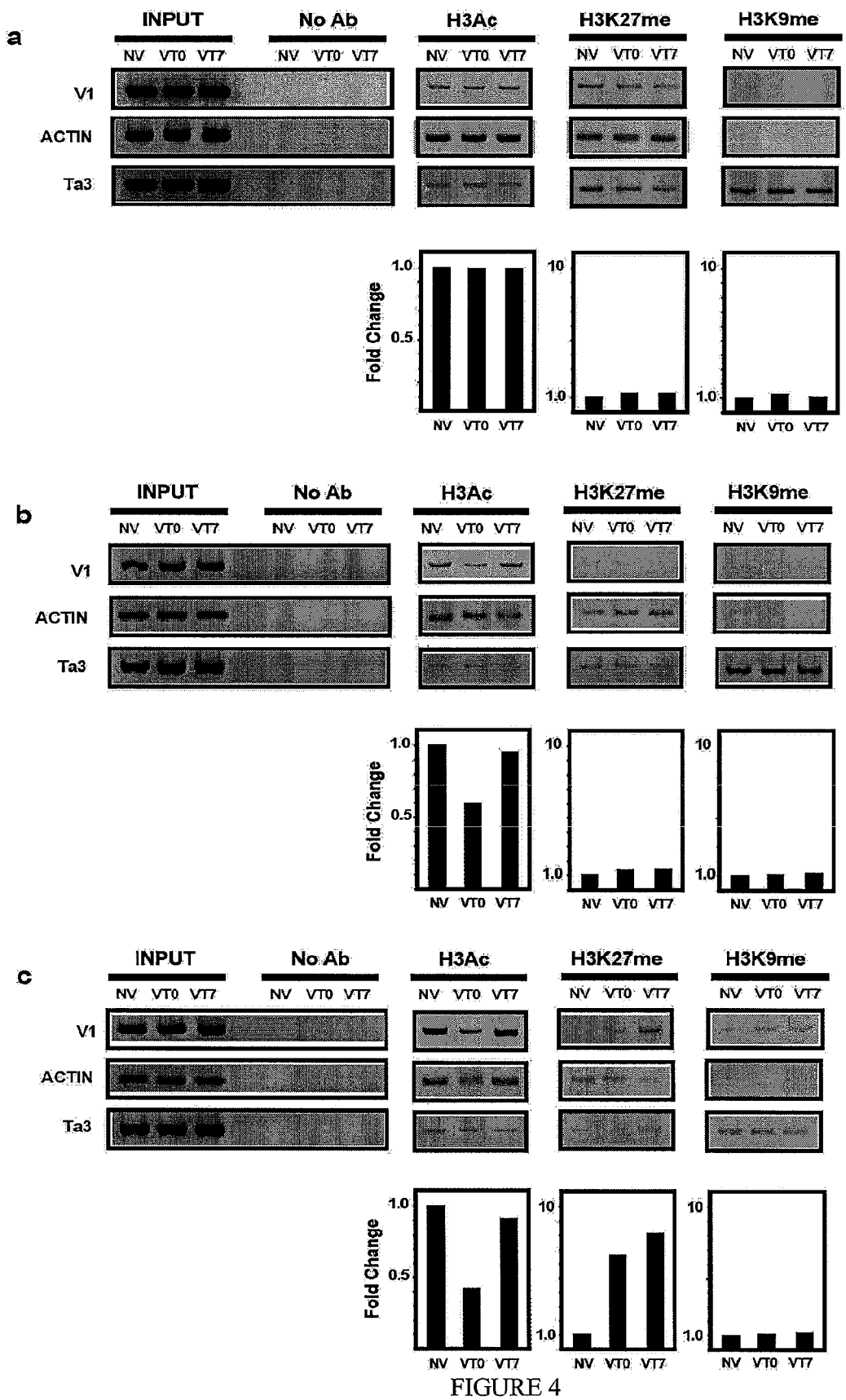
FIG. 4. Chromatin Immunoprecipitation (ChIP) assays in vernalization mutants. ChIP assays and designations are described in FIG. 3 Genotypes are vin3 (a), vrn2 (b) and vrn1 (c).

A candidate modification for the maintenance of vernalization-mediated FLC repression is H3 dimethylation at Lys 9[19]. Indeed the inventors found that in wild type, dimethylation levels at Lys 9 of H3 in chromatin of the FLC promoter and intron regions (P1 and V1) increase during vernalization and this increase is maintained after vernalization (FIG. 3b). In vin3, as well as in vrn1 and vrn2, the vernalization-mediated increase in H3 Lys 9 dimethylation does not occur (FIG. 4). The inventors also observe that in wild type the level of dimethylation at Lys 27 of H3 increases during and after vernalization (FIG. 3b). Interestingly, the H3 Lys 27 dimethylation increase occurs in vrn1 but not in vrn2 (FIG. 4b,c) indicating that VRN1 is not required for H3 Lys27 dimethylation and that H3 Lys 27 dimethylation alone is not sufficient to maintain FLC repression. The lack of both H3 Lys 9 and Lys 27 dimethylation in vrn 2 indicates that VRN2 activity is required for both dimethylations, whereas VRN1 activity is necessary for H3 Lys 9 dimethylation. VRN2 homologs in Drosophila and human (SUPPRESSOR OF ZESTE, Su(z) 12) are involved in H3 methylation[18] indicating that the role of this type of polycomb group protein in gene silencing is evolutionary conserved.

F. Direct Interaction of VIN3 with the FLC Locus

To address whether VIN3 can interact directly with the FLC locus, the inventors evaluated whether VIN3 antiserum could precipitate FLC chromatin (FIG. 3c). Precipitation of chromatin from vernalized plants with VIN3 antiserum greatly enriched for FLC compared to the pre-immune control. In addition, VRN1 antiserum greatly enriched for FLC chromatin compared to the pre-immune control. The regions of the promoter (P1) and the intron (V1) were enriched in these immunoprecipitations to a much greater extent than the 3' end (U1) of FLC. Thus the regions of FLC chromatin with which VIN3 and VRN1 interact in immunoprecipitation experiments correspond to the regions of FLC chromatin in which changes in histone modification occur. The interaction of VIN3 and VRN1 with the 5' promoter and first intron regions and the vernalization-mediated histone modifications of these regions are consistent with the observation that these regions are required for a proper vernalization response[21] and that a DNase 1-hypersensitive site in the intron region becomes insensitive after vernalization[11].

The epigenetic nature of vernalization was first recognized as a memory of winter in which the competence of an apical meristem to initiate flowering persists through mitotic cell divisions[22,23]. The inventors' results provide a framework for the molecular basis of vernalization in Arabidopsis. The establishment of FLC silencing (and FLC-independent aspects of the vernalized state) requires the induction of VIN3 expression by exposure to prolonged cold. VIN3 expression is necessary for de-acetylation of FLC which in turn leads to histone methylation and the formation of mitotically stable heterochromatin at the FLC locus by a process involving VRN1 and VRN2. VIN3 is induced by cold only in tissues (root and shoot apices) in which vernalization occurs, and the spatial restriction of VIN3 is likely to contribute to the restriction of the vernalization process to these tissues.

VRN1 and VRN2 are constitutively expressed[11,12], and the recruitment of VRN1 and VRN2 to target genes such as FLC during vernalization is likely to require a factor to provide specificity. The spatial expression pattern and cold-specific induction of VIN3 and the interaction of VIN3 with FLC chromatin indicates that VIN3 could be part of a transiently acting complex that leads to the initial establishment of target gene repression during vernalization. Consistent with this model, VIN3 is clearly the most upstream component of vernalization so far identified because vin3 is the only mutant in which FLC repression is blocked during cold exposure, and in which no histone modifications are detected during vernalization. Moreover, VIN3 is induced in vrn1 and vrn2, and VIN3-mediated FLC silencing during cold exposure occurs in vrn1 and vrn2.

The additional components that interact with VIN3, and VRN1 and VRN2, to repress FLC during and after vernalization are not known. One component may be an ENHANCER OF ZESTE like protein. In human and *Drosophila*, ENHANCER OF ZESTE (E(z)) acts as a histone methyl transferase in a complex with the VRN 2 homolog Su(z)12, and this complex is involved in polycomb complex-mediated gene repression[18]. MEDEA, CURLY LEAF and EZA 1 are the closest relatives of E(z) in *Arabidopsis*[24]. Lesions in CURLY LEAF cause ectopic expression of the floral homeotic gene AGAMOUS[24] and do not affect the vernalization process (not shown). It is possible that MEDEA or EZA 1 plays a role in vernalization, or that there is redundancy among E(z) relatives in this process, or that other proteins are involved in vernalization-mediated histone methylation.
Methods:

Plant Materials: The parental FRI-Sf2 in Columbia was previously described[3]. pSKI015 T-DNA[27] was used for T-DNA insertional mutagenesis of this line and fast-neutron mutagenesis was as described[4].

Mapping: A Landsberg erecta line into which was introgressed FRI-Sf2 & FLC-Col[3] was crossed to vin3-1, vin3-2, vin3-3 which are in the FRI-Sf2 in Columbia background to create mapping populations. 2345 individual F2 plants were used to localize VIN3.

RNA Analyses: RNA analyses were performed as described for blotting[28] and RT-PCR[29].

Chromatin immunoprecipitation (ChIP) assays: Formaldehyde cross-linked plant materials were used for ChIP assays as described[30]. Anti-acetyl-histone H3, anti-dimethyl-histone H3[Lys9] and anti-dimethyl-histone H3 [Lys27] antibodies from Upstate Biotechnology (Waltham, Mass. USA) were used for precipitation. Rabbit polyclonal antibodies to VRN1 and VIN3 were prepared by Covance(Denver, Pa. USA) against synthetic peptides SSQGNCVVYLPETTSA (VIN3)(SEQ. ID NO:7) and AFSVYIFNLSHSEIN (VRN1) (SEQ. ID NO:8) and were conjugated to keyhole limpet hemocyanin. Three pairs of primers that amplified the following regions of the FLC, locus were used to assess immunoprecipitation enrichment by PCR. The regions of the primer sets (P1, V1 and U1), relative to the start of transcription, are: P1(−495 to −470 and −222 to −197), V1 (+1436 to +1461 and +1699 to +1724), and U1 (+5805 to +5830 and +6019 to +6044).

G. VIN3-Mediated Histone Deacetylation of FLC Locus is Directed to FLC Intron 1

A 289-bp region (from +1328 to +1616, set forth herein as SEQ ID NO:4) of FLC Intron I is necessary for switching off FLC expression by vernalization. SEQ ID No. 5 contains the cDNA sequence for the FLC locus and SEQ ID No. 6 sets forth the genomic DNA for the FLC locus. Normally FLC will be switched off after vernalization; however, an FLC transgene in which this 289-bp region was deleted is still highly expressed after vernalization. Note however that it is possible that some of the region required to switch off a gene after vernalization may reside outside of the 289-bp region. Therefore the inventors tested deletions around the 289-bp region. The inventors find that a deletion extending to from 1079 to 1326 did not prevent vernalization and on the other side a deletion from 1617 to 1976 did not prevent vernalization. Thus one needs to note not only the 289-bp deletion (from +1328 to +1616) but also the other deletions that did not affect vernalization to conclude that the vernalization-responsive region resides between 1327 and 1616.

H. FLC Intron 1 directs Epigenetic Change of an Unrelated Gene.

The inventors also tested whether part of FLC Intron I is sufficient to switch off a reporter gene. A 1.8-kb fragment (from +197 to +2035) of FLC Intron I was inserted in an intron of a recombinant GUS (β-glucuronidase) reporter gene driven by 3.0-kb SPINDLY promoter. Without vernalization, GUS was very well expressed in *Arabidopsis* seedlings, but GUS was switched off after vernalization. The inventors used a portion of Intron 1 beyond that set forth in SEQ ID NO:4. The inventors chose the SPINDLY promoter for no particular reason except that it was a gene that is expressed in the same region as FLC and the native SPINDLY gene as well as the SPINDLY promoter fused to the GUS reporter gene (without the part of FLC) is not switched off after vernalization. This example demonstrates VIN3-mediated epigenetic change may be directed to non-FLC genes modified to contain relevant FLC Intron 1 and is illustrative of the robustness of methods for conferring epigenetic change described and claimed herein.

Those skilled in the art will recognize, or be able to ascertain using no more then routine experimentation, numerous equivalents to the specific polypeptides, nucleic acids, methods, assays and reagents described herein. Such equivalents are considered to be within the scope of this invention and covered by the following claims. All publications, patents, and patent applications cited herein are hereby incorporated by reference in their entirety for all purposes.

V. REFERENCES (1) Chouard, P. Vernalization and its relations to dormancy. Annu. Rev. Plant Physiol. 11, 191-238 (1960).
(2) Michaels, S. & Amasino, R. Memories of winter: vernalization and the competence to flower. Plant Cell and Environment 23, 1145-1154 (2000).
(3) Lee, I., Michaels, S. D., Masshardt, A. S. & Amasino, R. M. The late-flowering phenotype of FRIGIDA and LUMINIDEPENDENS is suppressed in the Landsberg erecta strain of *Arabidopsis*. Plant Journal 6, 903-909 (1994).
(4) Michaels, S. & Amasino, R. FLOWERING LOCUS C encodes a novel MADS domain protein that acts as a repressor of flowering. Plant Cell 11, 949-956 (1999).
(5) Sheldon, C. C. et al. The FLF MADS Box Gene. A repressor of flowering in *Arabidopsis* regulated by vernalization and methylation. Plant Cell 11, 445-458 (1999).
(6) Sheldon, C. C., Rouse, D. T., Finnegan, E. J., Peacock, W. J. & Dennis, E. S. The molecular basis of vernalization: the central role of FLOWERING LOCUS C (FLC). Proc Natl Acad Sci USA 97, 3753-3758 (2000).
(7) Michaels, S. D. & Amasino, R. M. Loss of FLOWERING LOCUS C activity eliminates the late-flowering phenotype of FRIGIDA and autonomous pathway mutations but not responsiveness to vernalization. Plant Cell 13, 935-942. (2001).
(8) Johanson, U. et al. Molecular analysis of FRIGIDA, a major determinant of natural variation in *Arabidopsis* flowering time. Science 290, 344-347 (2000).
(9) Gazzani, S., Gendall, A. R., Lister, C. & Dean, C. Analysis of the Molecular Basis of Flowering Time Variation in *Arabidopsis* Accessions. Plant Physiol. 132, 1107-1114 (2003).
(10) Michaels, S. D., He, Y., Scortecci, K. C. & Amasino, R. M. Attenuation of FLOWERING LOCUS C activity as a mechanism for the evolution of summer-annual

(11) Gendall, A. R., Levy, Y. Y., Wilson, A. & Dean, C. The VERNALIZATION 2 gene mediates the epigenetic regulation of vernalization in *Arabidopsis*. Cell 107, 525-535 (2001).

(12) Levy, Y. Y., Mesnage, S., Mylne, J. S., Gendall, A. R. & Dean, C. Multiple roles of *Arabidopsis* VRN1 in vernalization and flowering time control. Science 297, 243-246 (2002).

(13) Simpson, G. G. & Dean, C. *Arabidopsis*, the Rosetta stone of flowering time? Science 296, 285-289 (2002).

(14) Fair, K. et al. Protein interactions of the MLL PHD fingers modulate MLL target gene regulation in human cells. Mol Cell Biol 21, 3589-3597(2001).

(15) Main, A. L., Harvey, T. S., Baron, M., Boyd, J. & Campbell, I. D. The three-dimensional structure of the tenth type III module of fibronectin: an insight into RGD-mediated interactions. Cell 71, 671-678 (1992).

(16) Wellensiek, S. J. Dividing cells as the locus for vernalization. Nature 195, 307-308 (1962).

(17) Burn, J. E., Bagnall, D. J., Metzger, J. D., Dennis, E. S. & Peacock, W. J. DNA Methylation, vernalization, and the initiation of flowering. Proc Natl Acad Sci USA 90, 287-291 (1993).

(18) Kuzmichev, A. R. D., Nishioka, K., Erdjument-Bromage, H., P, T. & Reinberg, D. Histone methyltransferase activity associated with a human multiprotein complex containing the enhancer of Zeste protein. Genes and Development 16, 2893-2905 (2002).

(19) Richards, E. J. & Elgin, S. C. Epigenetic codes for heterochromatin formation and silencing: rounding up the usual suspects. Cell 108, 489-500 (2002).

(20) Kehle, J. et al. dMi-2, a hunchback-interacting protein that functions in polycomb repression. Science 282, 1897-1900 (1998).

(21) Sheldon, C. C., Conn A. B., Dennis E. S. & Peacock W. J. Different regulatory regions are required for the vernalization-induced repression of FLOWERING LOCUS C and for the epigenetic maintenance of repression. Plant Cell 14, 2527-2537 (2002).

(22) Lang, A. & Melchers, G. Vernalisation and devernalisation bei einer zweijahrigen pflanze. Z. Naturforsch. 2b, 444-449 (1947).

(23) Lang, A. Physiology of flower initiation. in Encyclopedia of Plant Physiology, Vol. 15 (Part 1) (ed. Ruhland, W.) 1371-1536 (Springer-Verlag, Berlin, 1965).

(24) Reyes, J. C., Hennig L. & Gruissem W. Chromatin-remodeling and memory factors. New regulators of plant development. Plant Physiol. 130, 1090-1101 (2002).

(25) Thomashow, M. F. So what's new in the field of plant cold acclimation? lots! Plant Physiol 125, 89-93 (2001).

(26) Gozani O. et al. The PHD finger of the chromatin-associated protein ING2 functions as a nuclear phosphoinositide receptor. Cell 114, 99-111 (2003).

(27) Weigel, D. et al. Activation tagging in *Arabidopsis*. Plant Physiol 122, 1003-1013. (2000).

(28) Michaels, S. D. & Amasino, R. M. The gibberellic acid biosynthesis mutant ga1-3 of *Arabidopsis thaliana* is responsive to vernalization. Dev Genet 25,194-198 (1999).

(29) Michaels, S. D. et al. AGL24 acts as a promoter of flowering in *Arabidopsis* and is positively regulated by vernalization. Plant J 33, 867-874 (2003).

(30) Johnson, L., Cao, X. & Jacobsen, S. Interplay between two epigenetic marks. DNA methylation and histone H3 lysine 9 methylation. Curr Biol 12, 1360-1367 (2002).

(31) Chouard, P: Vernalization and its relations to dormancy. Annu. Rev. Plant Physiol. 1960, 11: 191-238.

(32) Lang A: Physiology of flower initiation. In Encyclopedia of Plant Physiology, vol 15, Edited by Ruhland W. Berlin: Springer-Verlag; 1965: 1371-1536.

(33) Wellensiek S J: Dividing cells as the locus for vernalization. Nature 1962195: 307-308.

(34) Wellensiek S J: Dividing cells as the prerequisite for vernalization. Plant Physiol 39: 832-835.

(35) Burn J E, Bagnall D J, Metzger J D, Dennis E S, Peacock W J: DNA methylation, vernalization, and the initiation of flowering. Proc Natl Acad Sci USA 1993, 90: 287-291.

(36) Grewal S I S, Moazed D: Heterochromatin and epigenetic control of gene expression. Science 2003, 301: 798-801.

(37) Gendall A R, Levy Y Y, Wilson A, Dean C: The VERNALIZATION 2 gene mediates the epigenetic regulation of vernalization in *Arabidopsis*. Cell 2001, 107: 525-535.

(38) Levy Y Y, Mesnage S, Mylne J S, Gendall A R, Dean C: Multiple roles of *Arabidopsis* VRN1 in vernalization and flowering time control. Science 2002, 297: 243-246.

(39) Sung S, Amasino R. Vernalization in *Arabdopsis thaliana* is mediated by the PHD-finger protein VIN 3. Nature 2003, in press.

(40) Aasland R, Gibson T J, Stewart A F: The PHD finger: Implications for chromatin-mediated transcription regulation. Trends. Biochem. Sci. 1995, 20: 56-59.

(41) Kuzmichev A, Reinberg D, Nishioka K, Erdjument-Bromage H, Tempst P, Reinberg D: Histone methyltransferase activity associated with a human multiprotein complex containing the enhancer of Zeste protein. Genes Dev. 2002, 16: 2893-2905.

(42) Reyes J. C. Henning L, Gruissem W. Chromatin-remodelling and memory factors. New regulators of plant development. Plant Physiol 2002, 130:1090-1101.

(43) Schultz D C, Ayyanathan K, Negorev D, Maul G G, Rauscher F J 3rd: SETDB1: a novel KAP-1-associated histone H3, lysine 9-specific methyltransferase that contributes to HP1-mediated silencing of euchromatin genes by KRAB zinc-finger proteins. Genes Dev. 2002, 16:919-932.

(44) Kotake T, Takada S, Nakahigashi K, Ohto M, Goto K: Arabdopsis TERMINAL FLOWER 2 gene encodes a heterochormatin protein 1 homolog and represses both FLOWERING LOCUS T and regulate flowering time and several floral homeotic genes. Plant Cell Physiol 2003, 44:555-564

What is claimed is:

1. An isolated nucleic acid selected from a group consisting of:
   (a) a nucleotide sequence encoding an amino acid sequence set forth in SEQ ID NO:3;
   (b) a nucleotide sequence set forth in SEQ ID NO:1; and
   (c) a nucleotide sequence set forth in SEQ ID NO:2.

2. A vector comprising the isolated nucleic acid according to claim 1.

3. A method of inducibly-conferring epigenetic repression on a target gene in a plant shoot or root apical meristem, comprising the steps of:
   (a) providing a plant containing: (1) the isolated nucleic acid encoding VIN3 according to claim 1 under control of an inducible promoter; and (2) a target gene comprising the nucleotide sequence set forth in SEQ ID NO:4 from Intron 1 of Flowering Locus C; and
   (b) inducing expression of said isolated nucleic acid encoding VIN3 whereby VIN3-mediated epigenetic repression of the target gene is effectuated.

4. The method according to claim 3 wherein repression of said target gene results in alleviation of a vernalization response in the plant.

5. The method according to claim 3 wherein said plant is a winter annual or a biennial plant.

6. The method according to claim 3 wherein said plant is a Cruciferous plant.

7. The method according to claim 3 wherein said target gene is Flowering Locus C (FLC).

* * * * *

SEQUENCE LISTING

<160> NUMBER OF SEQ ID NOS: 6

<210> SEQ ID NO 1
<211> LENGTH: 1803
<212> TYPE: DNA
<213> ORGANISM: Arabidopsis thaliana

<400> SEQUENCE: 1

| | | |
|---|---|---|
| atggattctt cttcgtttga agataatgaa tgcattgaga cttgtaaacc aaacgttttg | 60 |
| aatgtaagtg aaaggagaga attgatccac gcattgtcta accagcctga agaagcttcg | 120 |
| gagcttttga attcatggag cagaaatgag atcatgaaga tcatatgtgc tgagatgggt | 180 |
| aaagaaagga agtacactgg tcttaacaaa ccaaagctca tagagaatct tctgaatctt | 240 |
| gtgtctcgtc ctcttggaga gacctcttgt tctgaccgta gaaactcgag gaagaaggag | 300 |
| aagaagatga tcggttacat catttgctgt gagaatttag cttgtagagc tgcgcttgga | 360 |
| tgcgatgata cgttttgcag aaggtgttct tgctgcatct gtcaaaagtt tgatgataat | 420 |
| aaggatccta gtttatggct tacttgtgat gcttgtggat cgtcttgtca tttggaatgt | 480 |
| ggtttgaagc aagataggta tgggattggg agtgatgatc ttgatggtag gttttattgc | 540 |
| gcgtattgcg gtaaagataa tgacttgctc ggatgctgga gaaaacaagt gaaggtggcg | 600 |
| aaagagacgc ggcgtgtgga tgtactttgt tatcgtcttt ctttaggaca gaagctgttg | 660 |
| agaggtacca cgaagtatcg gaatctgttg gaacttatgg atgaggcggt gaagaagctc | 720 |
| gaaggtgatg tgggtccgtt gtcgggttgg gccatgaaga tggctcgagg catcgtcaat | 780 |
| agactttctt cgggtgtgca tgtccagaag ctgtgttctc aggcaatgga agctctggac | 840 |
| aaagtggtct caccatcaga atctgtttca ggacaaggtg acaagatgac cgtgagagta | 900 |
| gaagagattc aagcaagatc agtcactgtg agagtagact ccgaggagcc gtcttcttct | 960 |
| acacaaaaca agatcacagg tttcaggttg ttttgtcgaa agtcgaagga cgaagaatgc | 1020 |
| tcgtctcagg ggaattgtgt tgtttatcta cctgagacga cgtctgccat ccaaggactt | 1080 |
| gaacccgaca ccgagttctg tctcagagtg gttttccttta acgaggaagg tgacttagat | 1140 |
| gagtctgagc ttcggttcac aacgttgaag gatgatggag atgaagctgg ggaccagcaa | 1200 |
| agcccttttga caaactcaag cagtggtctt tgtagtaatc catctttacc agaagatgaa | 1260 |
| tctaataatg tcaataaaag ctgcagcaaa ggaaatggtg acaaggacaa cactgaacac | 1320 |
| tgtagtgcag agaagtaga atctgagctt gaagaagaga ggcttgtaaa gaggaaagca | 1380 |
| aacaagatag atggaagaga cttgcttgta acaccctgca agagagatat ttataaagga | 1440 |
| aagcaaggag ggaataaaag attcaaatca agaacagtat ccttgaacga gaaacctgag | 1500 |
| atcaataatg ccgcaaatgg agtaggagat aaagacttgg gtcatattgt taagacgatt | 1560 |
| agatgtttag aggaagaagg acatatagac aagagttttta gggaaaggtt cttgacatgg | 1620 |
| tatagcttaa gagctactca ccgagaagta agagttgtga agatctttgt tgagacgttt | 1680 |
| atggaggatc tgtcttcttt gggacaacag cttgtggata cattctcaga agtatactg | 1740 |
| agtaagagat catcgacaaa tggtgtagta cctgctggga tctgcctcaa gctttggcat | 1800 |
| taa | 1803 |

<210> SEQ ID NO 2
<211> LENGTH: 2232
<212> TYPE: DNA
<213> ORGANISM: Arabidopsis thaliana

<400> SEQUENCE: 2

```
atggattctt cttcgtttga aggtacgata ttttctcgac gtgaacgtct ctctcactgt      60
tcctagtttc atgcgtttta ggtcgttaac acgacgacgt ttttacacaa tatcaacaaa     120
cgttttattt ctcgcattgg attcgtcgtc attgttgata tttcgtttct ggttgttga     180
gattcattca aagttttata cttttgatca tttttacccc aaaaagagtc agaatctgtg     240
atcctctcct ttttatcttg aggagaatct agggctaaag gattggtctt ttatggtgca     300
gataatgaat gcattgagac ttgtaaacca aacgttttga atgtaagtga aaggagagaa     360
ttgatccacg cattgtctaa ccagcctgaa gaagcttcgg agcttttgaa ttcatggagc     420
agaaatgaga tcatgaagat catatgtgct gagatgggta agaaaggaa gtacactggt      480
cttaacaaac caaagctcat agagaatctt ctgaatcttg tgtctcgtcc tcttggagag     540
acctcttgtt ctgaccgtag aaactcgagg aagaaggaga agaagatgat cggttacatc     600
atttgctgtg agaatttagc ttgtagagct gcgcttggat gcgatgatac gttttgcaga     660
aggtgttctt gctgcatctg tcaaaagttt gatgataata aggatcctag tttatggctt     720
acttgtgatg cttgtggatc gtcttgtcat ttggaatgtg gtttgaagca agataggtat     780
gggattggga gtgatgatct tgatggtagg ttttattgcg cgtattgcgg taaagataat     840
gacttgctcg ggtaaggatc tttagatatt gaaatctatg gatatactac aatgaaaaga     900
gaatgtaatg taatgtgtgt gtatgcgagt gcttacagat gctggagaaa acaagtgaag     960
gtggcgaaag agacgcggcg tgtggatgta ctttgttatc gtctttcttt aggacagaag    1020
ctgttgagag gtaccacgaa gtatcggaat ctgttggaac ttatggatga ggcggtgaag    1080
aagctcgaag gtgatgtggg tccgttgtcg ggttgggcca tgaagatggc tcgaggcatc    1140
gtcaatagac tttcttcggg tgtgcatgtc cagaagctgt gttctcaggc aatggaagct    1200
ctggacaaag tggtctcacc atcagaatct gtttcaggac aaggttagtg tgttcataca    1260
ttactttggt tttaaaaccg aagatgttga ctttagttcc tgttaggtga caagatgacc    1320
gtgagagtag aagagattca agcaagatca gtcactgtga gagtagactc cgaggagccg    1380
tcttcttcta cacaaaacaa gatcacaggt ttcaggttgt tttgtcgaaa gtcgaaggac    1440
gaagaatgct cgtctcaggg gaattgtgtt gtttatctac ctgagacgac gtctgccatc    1500
caaggacttg aacccgacac cgagttctgt ctcagagtgg tttcctttaa cgaggaaggt    1560
gacttagatg agtctgagct tcggttcaca acgttgaagg atgatggaga tgaagctggg    1620
gaccagcaaa gccctttgac aaactcaagc agtggtcttt gtagtaatcc atctttacca    1680
gaagatgaat ctaataatgt caataaaagc tgcagcaaag gaaatggtga caaggacaac    1740
actgaacact gtagtgcagg agaagtagaa tctgagcttg aagaagagag gcttgtaaag    1800
aggaaagcaa acaagataga tggaagagac ttgcttgtaa caccctgcaa gagagatatt    1860
tataaaggaa agcaaggagg gaataaaaga ttcaaatcaa gaacagtatc cttgaacgag    1920
aaacctgaga tcaataatgc cgcaaatgga gtaggagata aagacttggg tcatattgtt    1980
aagacgatta gatgtttaga ggaagaagga catatagaca agagtttag ggaaaggttc     2040
ttgcatggt atagcttaag agctactcac cgagaagtaa gagttgtgaa gatctttgtt    2100
gagacgttta tggaggatct gtcttctttg ggacaacagc ttgtggatac attctcagaa    2160
agtatactga gtaagagatc atcgacaaat ggtgtagtac ctgctgggat ctgcctcaag    2220
cttttggcatt aa                                                          2232
```

<210> SEQ ID NO 3
<211> LENGTH: 600
<212> TYPE: PRT
<213> ORGANISM: Arabidopsis thaliana

<400> SEQUENCE: 3

```
Met Asp Ser Ser Ser Phe Glu Asp Asn Glu Cys Ile Glu Thr Cys Lys
1               5                   10                  15

Pro Asn Val Leu Asn Val Ser Glu Arg Arg Glu Leu Ile His Ala Leu
            20                  25                  30

Ser Asn Gln Pro Glu Glu Ala Ser Glu Leu Leu Asn Ser Trp Ser Arg
        35                  40                  45

Asn Glu Ile Met Lys Ile Ile Cys Ala Glu Met Gly Lys Glu Arg Lys
50                  55                  60

Tyr Thr Gly Leu Asn Lys Pro Lys Leu Ile Glu Asn Leu Leu Asn Leu
65                  70                  75                  80

Val Ser Arg Pro Leu Gly Glu Thr Ser Cys Ser Asp Arg Arg Asn Ser
                85                  90                  95

Arg Lys Lys Glu Lys Lys Met Ile Gly Tyr Ile Ile Cys Cys Glu Asn
            100                 105                 110

Leu Ala Cys Arg Ala Ala Leu Gly Cys Asp Asp Thr Phe Cys Arg Arg
        115                 120                 125

Cys Ser Cys Cys Ile Cys Gln Lys Phe Asp Asp Asn Lys Asp Pro Ser
    130                 135                 140

Leu Trp Leu Thr Cys Asp Ala Cys Gly Ser Ser Cys His Leu Glu Cys
145                 150                 155                 160

Gly Leu Lys Gln Asp Arg Tyr Gly Ile Gly Ser Asp Asp Leu Asp Gly
                165                 170                 175

Arg Phe Tyr Cys Ala Tyr Cys Gly Lys Asp Asn Asp Leu Leu Gly Cys
            180                 185                 190

Trp Arg Lys Gln Val Lys Val Ala Lys Glu Thr Arg Arg Val Asp Val
        195                 200                 205

Leu Cys Tyr Arg Leu Ser Leu Gly Gln Lys Leu Leu Arg Gly Thr Thr
    210                 215                 220

Lys Tyr Arg Asn Leu Leu Glu Leu Met Asp Glu Ala Val Lys Lys Leu
225                 230                 235                 240

Glu Gly Asp Val Gly Pro Leu Ser Gly Trp Ala Met Lys Met Ala Arg
                245                 250                 255

Gly Ile Val Asn Arg Leu Ser Ser Gly Val His Val Gln Lys Leu Cys
            260                 265                 270

Ser Gln Ala Met Glu Ala Leu Asp Lys Val Val Ser Pro Ser Glu Ser
        275                 280                 285

Val Ser Gly Gln Gly Asp Lys Met Thr Val Arg Val Glu Glu Ile Gln
    290                 295                 300

Ala Arg Ser Val Thr Val Arg Val Asp Ser Glu Pro Ser Ser Ser
305                 310                 315                 320

Thr Gln Asn Lys Ile Thr Gly Phe Arg Leu Phe Cys Arg Lys Ser Lys
                325                 330                 335

Asp Glu Glu Cys Ser Ser Gln Gly Asn Cys Val Val Tyr Leu Pro Glu
            340                 345                 350

Thr Thr Ser Ala Ile Gln Gly Leu Glu Pro Asp Thr Glu Phe Cys Leu
        355                 360                 365

Arg Val Val Ser Phe Asn Glu Glu Gly Asp Leu Asp Glu Ser Glu Leu
    370                 375                 380
```

```
Arg Phe Thr Thr Leu Lys Asp Asp Gly Asp Glu Ala Gly Asp Gln Gln
385                 390                 395                 400

Ser Pro Leu Thr Asn Ser Ser Gly Leu Cys Ser Asn Pro Ser Leu
            405                 410                 415

Pro Glu Asp Glu Ser Asn Asn Val Asn Lys Ser Cys Ser Lys Gly Asn
                420                 425                 430

Gly Asp Lys Asp Asn Thr Glu His Cys Ser Ala Gly Glu Val Glu Ser
                435                 440                 445

Glu Leu Glu Glu Glu Arg Leu Val Lys Arg Lys Ala Asn Lys Ile Asp
    450                 455                 460

Gly Arg Asp Leu Leu Val Thr Pro Cys Lys Arg Asp Ile Tyr Lys Gly
465                 470                 475                 480

Lys Gln Gly Gly Asn Lys Arg Phe Lys Ser Arg Thr Val Ser Leu Asn
                485                 490                 495

Glu Lys Pro Glu Ile Asn Asn Ala Ala Asn Gly Val Gly Asp Lys Asp
                500                 505                 510

Leu Gly His Ile Val Lys Thr Ile Arg Cys Leu Glu Glu Glu Gly His
    515                 520                 525

Ile Asp Lys Ser Phe Arg Glu Arg Phe Leu Thr Trp Tyr Ser Leu Arg
530                 535                 540

Ala Thr His Arg Glu Val Arg Val Val Lys Ile Phe Val Glu Thr Phe
545                 550                 555                 560

Met Glu Asp Leu Ser Ser Leu Gly Gln Gln Leu Val Asp Thr Phe Ser
                565                 570                 575

Glu Ser Ile Leu Ser Lys Arg Ser Ser Thr Asn Gly Val Val Pro Ala
                580                 585                 590

Gly Ile Cys Leu Lys Leu Trp His
                595                 600

<210> SEQ ID NO 4
<211> LENGTH: 290
<212> TYPE: DNA
<213> ORGANISM: Arabidopsis thaliana

<400> SEQUENCE: 4
catagatttg cctcatattt atgtgattgt atatcaatta tcgcccttaa tcttatcatc      60
gttgtgttca tttatgactt tgttcctatt cgttaaaatt gacaatccac aacctcaatc     120
ttttgttgtg aaaatcgaca atcacacaac ctttgtatct tgtgtctttt gtcacacaac     180
ctttgtatct tgtgtctttt gtcatggaaa ttgtcattca cacagccttg tttctttggt     240
gcctctagga aattgaaaat cccacaacac ttgtcttcat gtaagaaata                290

<210> SEQ ID NO 5
<211> LENGTH: 591
<212> TYPE: DNA
<213> ORGANISM: Arabidopsis thaliana

<400> SEQUENCE: 5
atgggaagaa aaaactaga atcaagcga attgagaaca aaagtagccg acaagtcacc       60
ttctccaaac gtcgcaacgg tctcatcgag aaagctcgtc agctttctgt tctctgtgac    120
gcatccgtcg ctcttctcgt cgtctccgcc tccggcaagc tctacagctt ctcctccggc    180
gataacctgg tcaagatcct tgatcgatat gggaaacagc atgctgatga tcttaaagcc    240
ttggatcatc agtcaaaagc tctgaactat ggttcacact atgagctact tgaacttgtg    300
```

-continued

```
gatagcaagc ttgtgggatc aaatgtcaaa aatgtgagta tcgatgctct tgttcaactg      360
gaggaacacc ttgagactgc cctctccgtg actagagcca agaagaccga actcatgttg      420
aagcttgttg agaatcttaa agaaaaggag aaaatgctga agaagagaaa ccaggttttg      480
gctagccaga tggagaataa tcatcatgtg ggagcagaag ctgagatgga gatgtcacct      540
gctggacaaa tctccgacaa tcttccggtg actctcccac tacttaatta g               591

<210> SEQ ID NO 6
<211> LENGTH: 5968
<212> TYPE: DNA
<213> ORGANISM: Arabidopsis thaliana

<400> SEQUENCE: 6
cgagaaaagg aaaaaaaaaa atagaaagag aaaacgctta gtatctccgg cgacttgaac       60
ccaaacctga ggatcaaatt agggcacaaa gccctctcgg agagaagcca tgggaagaaa      120
aaaactagaa atcaagcgaa ttgagaacaa agtagccga caagtcacct tctccaaacg       180
tcgcaacggt ctcatcgaga aagctcgtca gctttctgtt ctctgtgacg catccgtcgc      240
tcttctcgtc gtctccgcct ccggcaagct ctacagcttc cctccggcg ataagtacgc       300 cttttcctta cctgggtttt catttgttcc ccctttatc ttctgttttg tgctctttta       360
cttttctgag aaaataaaaa taaaaaaaca attaatatac cgtttggttt ttttccggcg      420
gatctcttgt tgtttctcgg ttctgtgttt gtttgtgttt tttctgcga ccatgataga       480 tacatgagat aaccaaattt aaggaagaac aatgtcgtga agaagctttt tagcttctta      540
cttttgttca tttctctctc tatttcttaa aaaaaaaaat tctgcatgga tttcattatt      600
tccttggaaa aaaattgcat gtcattcacg atttgtttga tacgatctga tgcgtgctcg      660
atgttgttga gtgaagtttc aagccatctt tgattgtttc ttacctttag agattcctta      720 agttttttgaa gagttaatta tatatcacaa gactaatgat taatgtctct tttcagagtg      780
attaaaattc attggatctc tcggatttgt atgcaatgca cttacgggag atctatagag      840
ttgctatggg gttaatgctg aacaatgtat atataccaca ttgtgcagct attgactata      900
taagactatt gttaatcttc tatgaattcc tatctttgct gtggacctat tacttggtga      960
ttatccaaat tagtgttttt aattgattca tattttcat acacagtagt tttgaatttt     1020
ggtagcttca aaaactcag cctcacaatt agtacttacc gcacatatgc tacttcagta      1080
acataatctg gttatcgatt gcgattcttt gaatcacaat cgtcgtgtgc tatatatata     1140 acacctttg ctgtacataa actggtctaa ttttagacta attaaatttc attgttctct      1200
tggatttgta tatgcacgtc cgggagattt ataaataaaa ttagtatgag gttaatggta     1260
aaaaggatca agaagtttgg ttttaaatgt aagccacatt aattgggaaa ctatgactaa     1320
aagatgaatt ggtaatatat acataatatt tttaacgaat ttctctcctt tttatgggat     1380
atgctattta agattgtcc aaaggtttat agtttcccac tcttgcagtt acacacatag      1440
atttgcctca tatttatgtg attgtatatc aattatcgcc cttaatctta tcatcgttgt     1500
gttcatttat gactttgttc ctattcgtta aaattgacaa tccacaacct caatcttttg     1560
ttgtgaaaat cgacaatcac acaacctttg tatcttgtgt cttttgtcac acaacctttg     1620
tatcttgtgt cttttgtcat ggaaattgtc attcacacag cctgtttct ttggtgcctc      1680 taggaaattg aaaatcccac aacacttgtc ttcatgtaag aaataccaac ctctttggta     1740
cggatctata tgaatcaat ataatcctat atataagttg tcaaaattga atctggtgta      1800
gtgtctacta caaccctcca atataataac caaatggttg tagtagtttg gccatgttgg     1860
```

```
tcaagatcgc tggccgattc tcacttgatg catactttgt taggatttgt tcaccoctag    1920 ttaggtccag ccttggaatt gtcgagacac ctgactagaa ctcctggtct taattatgat    1980
ttaataaaga agaagccttt tagaacgtgg aaccettagt tactcagtta ctcttttgc     2040 atacttaggt tgatgcaaag agcttaactt cacaatagga ctgatatcta ttaacaaaac    2100
aaattaagtg aagttttgtc aaaattgttg gatcttctag gtcaatatgt agtttagttt    2160
ttatctgtct tagtcgcttc cttctatgga agatatattt atagatatgt gtgataagtt    2220
tcctactaat attagttagt gtaacttcaa gggcagaaaa ctctttactt ttattgcttg    2280
attaatttgg ggtttaaata taggaaattg gaacctcaca gtttctataa acgagtaagt    2340
aattgaatgt gaaataacaa aatggaagac cggcttccta ttcttaggag tcttttgata    2400
tttgcaaaaa aaacatatac aatagaaata tgagttttgt ctaagactcg gtccatgtat    2460
ttggagtttg gcttcctcat acttatggtt atctggttac cgccacatca tcattatcat    2520
cttatgggtc atcaatacta gctctatcgc tggaaaaaac cttgtcctca aggttcattg    2580
aaaaatccga aaagttttct cgtatatgtt gatatggtat tacttacaaa caaagagctg    2640
atgttaccaa ttttgacacg agattactaa tgaactcatg aaagaggcgt ttttaaaaaa    2700
ttctttttaa aactgggata caaaaagaaa agaggtaact aataatttga taccattgtt    2760
cgtagtcctg atcaaatgtt ataagggtaa acatgataga aaatagaggg taaataggtt    2820
ttgttcttat aatggttttg ataacacgct ttgtaaagga tataggtgtt ttttgatgct    2880
aaaagttgtg gtatggatca aaaccaaaat ggaagctctg aatctctgat agaggttgca    2940
attagaatta tataagttaa tttgcaaatg aattggaagc agtcttccac tatttgctat    3000
tgttagggaa gtctttcagt taatttcaga aaattaagag aaatatgact ttctagactc    3060
agtctgtgta cttggaattt tacttcggtt tacttccatg tcatcacatt gtggctcatc    3120
aatatatgtg tgtatataca ttcatgagta tatatgattt ctggaaaaat aaaaattgct    3180
tgtttgcatt taagattggg gctgcgttta catttatat tgcatcaatt atttcaacat     3240
agattcacaa acataaatgc atagaaacaa tctggacagt agaggcttat gtttagggtt    3300
cttatgtacc ttaactagtt tgactttaag ttaatcaaag ccagcgctat cactaaactt    3360
tatctgtatg cctttgtatg acttttcttt gagggaaaat gtcattttca atctgccgaa    3420
atatataata aatacatgtt agcccacata attcattgga taactaatct ttgagcaatt    3480
tttggtaaat gttttggttc ttttctttc ttgagagaga aaaaaaatat cagatattat     3540
taaatattgc ttacaaagct aagaacaagt taaaacttt ttgaaaaagt ggaaattcag     3600
atgtgctact gcttaaacat gaatattaag attattgttt ttctgaaatg ttacgaatac    3660
tagcgtgtta tatatatgta aaaggtaagg tgttctctca atgtttcata gtttccagtg    3720 gcctttcaa gggttagcta gtagttttga tcctaacata tttttatttt ttttgtcatc     3780
tctccagcct ggtcaagatc cttgatcgat atgggaaaca gcatgctgat gatcttaaag    3840
ccttggtaat acaaacattt tgaatctttt ccctgatgga gttttataag gcgtaaattt    3900
actattagtt tgccgagtga tcctaaatat aaaatgaggt ggtggctcca catgcattat    3960
gcataccgca attttcatag cccttgtctt ttaccgcttc ttctgtccct ttttcatggg    4020
caggatcatc agtcaaaagc tctgaactat ggttcacact atgagctact tgaacttgtg    4080
gataggttag tactactaac taagactata tttgctctcc acctttgatt acaaaggaat    4140 tagtttttt tttgtcaaac tatgaatata tgcagcaagc ttgtgggatc aaatgtcaaa     4200
```

```
aatgtgagta tcgatgctct tgttcaactg gaggaacacc ttgagactgc cctctccgtg    4260
actagagcca agaaggtaag ttgatttcgt aatgtctact cctttctgaa ttttgtttgc    4320
tgagaacaac cgtgctgctt ttgtttgttg cagaccgaac tcatgttgaa gcttgttgag    4380
aatcttaaag aaaaggtcag atatttgcta ccaattttat tgtacatcag atatatcctc    4440
ttctgtgttg tctctgttac tttaagtctg cttaacgagc ttgcacacat atttgcaact    4500
ttcttcatat gttttggatt ccaaattctg aagttgttag gtttagaaac ttgatcggta    4560
attgctgaac attttgatct ttaaatcagg agaaaatgct gaaagaagag aaccaggttt    4620
tggctagcca ggtaacgaaa gctacatttc ctaaaaatat atatgcataa ctaataagca    4680
ctgcgtgttg tgtgtccaat gtccatgtac atggacatag atacacactc ttatgcttgc    4740
agatatatat atatatatat atagtcagtg catttcaatc attcactagt tagcactttc    4800
ctgtcttgta tagttgtatt ctagacaatt cttctcaaga ttagggcatt ttggttgttg    4860
gtagtttggt ttattagggt tagtgagatt attactgaat aagaacagaa ttttgataac    4920
ggctggttag agttaaggga aatcagatga agttattttt ttatttttta tcgagtataa    4980
attacatgat tgctatatca ttttactaaa ttaagaaaaa aaaattccgg ttgttggaca    5040
taactaggtt ttggttcttc ttcttcgttt ttttcatgtt aaagtgttta attaggtttt    5100
ggttcatttg gagatttatg aaccttttat agtctggtta agtctgggtt tggtagagat    5160
tcaataagat ttcttgattc tctttcaggt tatggtctgg ttcagtctag tttagttcaa    5220
tattggtttc cttgaaggtt gtgtaaacgt tgtctatatt taagttaatc accttttaac    5280
caaaaaaaaa agtttatgga ccgattagtt tttttttttt tgttttttttt gttatggtta    5340 ggtttggatc cgagtggctc agttccaact ccaagtgtct agaagtagtg ctacttttac    5400
atgctatata taggttagat tataaattat aaactggtaa aagattatag atactgcttc    5460
caaacttaaa agcttaaaca taaagaacac acaaattatg agaaacataa ccttctgtag    5520 tgtttttttaa tggttgttat ttggtggtgt gaaaaagata ttccttggat agaagacaaa    5580
aagagaaagt gaatagtgat tttgacctat gattatcgta cagatggaga ataatcatca    5640
tgtgggagca gaagctgaga tggagatgtc acctgctgga caaatctccg acaatcttcc    5700
ggtgactctc ccactactta attagccacc ttaaatcggc ggttgaaatc aaaatccaaa    5760
acatatataa ttatgaagaa aaaaaaaata agatatgtaa ttattccgct gataagggcg    5820
agcgtttgta tatcttaata ctctctcttt ggccaagaga ctttgtgtgt gatacttaag    5880
tagacggaac taagtcaata ctatctgttt taagacaaaa ggttgatgaa ctttgtacct    5940
tattcgtgtg agaattgcat cgagatct                                      5968
```